United States Patent [19]

Kashima et al.

[11] Patent Number: 5,716,950
[45] Date of Patent: Feb. 10, 1998

[54] DIAZACYCLOALKANEALKYLSULFONAMIDE DERIVATIVES

[75] Inventors: Kenichi Kashima, Fujiidera; Yoshinobu Akimoto, Uji; Yasuhiko Sakamoto, Habikino; Hirohiko Sakamoto, Ikoma-gun; Kayo Yokode, Yamatokoriyama; Toshimi Sakurai, Nara; Takeshi Takeno, Takatsuki; Shigetaka Takemura, Osaka; Hiroichi Nagai, Gifu, all of Japan

[73] Assignee: Nippon Shoji Kabushiki Kaisha, Osaka, Japan

[21] Appl. No.: 530,100

[22] PCT Filed: Jan. 9, 1995

[86] PCT No.: PCT/JP95/00008

§ 371 Date: Nov. 20, 1995

§ 102(e) Date: Nov. 20, 1995

[87] PCT Pub. No.: WO95/19345

PCT Pub. Date: Jul. 20, 1995

[30] Foreign Application Priority Data

Jan. 14, 1994 [JP] Japan ................... 6-002609

[51] Int. Cl.$^6$ .............. A61K 31/55; A61K 31/495; C07D 295/12; C07D 401/06
[52] U.S. Cl. .............. 514/218; 514/252; 514/255; 540/575; 544/360; 544/396
[58] Field of Search ................. 544/360, 396; 540/575; 514/218, 252, 255

[56] References Cited

U.S. PATENT DOCUMENTS

| | | | |
|---|---|---|---|
| 3,267,104 | 8/1966 | Hermans et al. | 544/396 |
| 4,795,752 | 1/1989 | Hattori et al. | 544/396 |
| 5,389,630 | 2/1995 | Sato et al. | 540/575 |
| 5,478,941 | 12/1995 | Cossement et al. | 544/396 |

FOREIGN PATENT DOCUMENTS

| | | |
|---|---|---|
| 558245 | 9/1993 | European Pat. Off. |
| 153280 | 7/1987 | Japan |
| 233670 | 9/1990 | Japan |

OTHER PUBLICATIONS

Abstract for JP153280 (Jul. 8, 1987).

Abstract for JP233670 (Sep. 17, 1990).

*Primary Examiner*—Emily Bernhardt
*Attorney, Agent, or Firm*—Jacobson, Price, Holman & Stern, PLLC

[57] ABSTRACT

A diazacycloalkanealkylsulfonamide derivative having the following formula [I]:

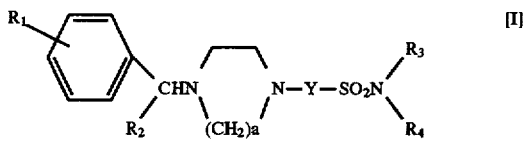

and pharmacologically acceptable salts thereof. The compounds have antiallergic activity with low antihistaminic activity and low toxicity and are useful as an medicament for preventing and treating diseases such as bronchial asthma, allergic rhinitis, atopic dermatitis, urticaria.

9 Claims, No Drawings

DIAZACYCLOALKANEALKYLSULFONAMIDE DERIVATIVES

FIELD OF THE INVENTION

This invention relates to novel diazacycloalkanealkylsulfonamide derivatives having excellent antiallergic activity and thereby are useful as an medicament for preventing and treating diseases such as bronchial asthma, allergic rhinitis, atopic dermatitis, urticaria and the like, and pharmacologically acceptable salts thereof.

PRIOR ART

Presently, some kinds of antihistaminic agents or antiallergic agents having diazacycloalkane-skeletal structure have been found, for example, 1-[(4-chlorophenyl) phenylmethyl]-4-methylpiperazine [generic name: Chlorcyclizine (Merck Index, 11th edition, 2078)], 1-[(4-chlorophenyl)phenylmethyl]-hexahydro-4-methyl-1H-1,4-diazepine [generic name: Homochlorcyclizine (Merck Index, 11th edition, 4653)]. Among diazacycloalkanealkylsulfonic acids, it is known that some compounds have accelerating activity of erythrocyte transformation and antiplatelet aggregation activity [Japanese Patent First Publication No. 233670/1990]. However, for example, as shown in Experiments hereinafter, a compound of Reference Example 4 did not show an antiallergic activity. Some of diazacycloalkane alkylsulfonamide derivatives are also known [Japanese Patent First Publication No. 153280/1987] and the compounds have calcium antagonistic activity and antiallergic activity. However, they have insufficient activity of suppressing passive cutaneous anaphylaxis (PCA).

Antiallergic agents have been used for treating diseases such as bronchial asthma, allergic dermal affection and allergic rhinitis. However, existing antiallergic agents, e.g. ketotifen, have some defects that drowsiness or sedation are caused by central nervous suppressing activity due to their strong antihistaminic side effects. With the object of removing these defects, various studies have been done until now, but no satisfactory result has been obtained.

DETAILED DESCRIPTION OF THE INVENTION

Under the circumstances, the present inventors have intensively studied, and as a resultant, have found that specific diazacycloalkanealkylsulfonamide derivatives have excellent antiallergic activity with low antihistaminic activity and low toxicity, and further they can readily be prepared.

The present invention provides diazacycloalkanealkylsulfonamide derivatives having the following formula [I]:

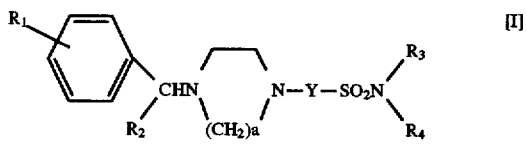

[wherein $R_1$ is hydrogen atom, lower alkyl, lower alkoxy, halogen atom, hydroxy, trifluoromethyl, nitro or amino; $R_2$ is phenyl which may optionally be substituted by 1 to 3 substituents on the phenyl ring selected from lower alkyl, lower alkoxy, halogen atom, hydroxy, trifluoromethyl, nitro and amino, or 2-pyridyl, 3-pyridyl or 4-pyridyl; a is 2 or 3; Y is alkylene; and $R_3$ and $R_4$ are the same or different and are each hydrogen atom, lower alkyl, lower hydroxyalkyl or cycloalkyl, or phenyl which may optionally be substituted by 1 to 3 substituents on the phenyl ring selected from lower alkyl, lower alkoxy, halogen atom, hydroxy, trifluoromethyl, nitro and amino] and pharmacologically acceptable salts thereof.

In the above formula [I], the lower alkyl expressed by $R_1$ denotes alkyl containing 1 to 4 carbon atoms which include methyl, ethyl, n-propyl, isopropyl, n-butyl, isobutyl and tert-butyl. Lower alkoxy expressed by $R_1$ denotes alkoxy containing 1 to 4 carbon atoms which include methoxy, ethoxy, n-propoxy, isopropoxy, n-butoxy, isobutoxy and tert-butoxy. Halogen atoms expressed by $R_1$ include chlorine, bromine, fluorine and iodine.

Lower alkoxy and halogen atoms as substituents on the phenyl ring in $R_2$ include the same groups as defined in the above $R_1$.

Alkylene expressed by Y denotes straight or branched chain alkylene containing 1 to 12 carbon atoms, and preferably to straight chain alkylene particularly containing 3 to 10 carbon atoms, more particularly 4 to 8 carbon atoms. For example, they include methylene, ethylene, propylene, butylene, pentylene, hexylene, heptylene, octylene, nonylene, decanylene, undecanylene and dodecanylene.

Lower alkyl expressed by $R_3$ and $R_4$ denotes alkyl containing 1 to 4 carbon atoms which include methyl, ethyl, n-propyl, isopropyl, n-butyl, isobutyl and tert-butyl. Lower hydroxyalkyl denotes hydroxyalkyl containing 1 to 4 carbon atoms such as hydroxymethyl, hydroxyethyl, hydroxypropyl, hydroxybutyl. Cycloalkyl denotes cycloalkyl containing 3 to 8 carbon atoms which include cyclopropyl, cyclobutyl, cyclopentyl, cyclohexyl, cycloheptyl, and cyclooctyl. Lower alkyl, lower alkoxy and halogen atoms as substituents on phenyl ring in $R_3$ and $R_4$ include the same groups defined in above $R_1$.

Preferred compounds of the present invention are the compounds of formula [I] wherein $R_1$ is hydrogen atom, alkyl containing 1 to 4 carbon atoms, alkoxy containing 1 to 4 carbon atoms, halogen atom, hydroxy, trifluorometyl, nitro or amino; $R_2$ is unsubstituted phenyl, phenyl substituted by 1 to 2 halogen atoms, 2-pyridyl or 4-pyridyl; a is 2; Y is alkylene containing 3 to 10 carbon atoms; and one of $R_3$ and $R_4$ is hydrogen atom and the other is hydrogen atom, alkyl containing 1 to 4 carbon atoms, hydroxyalkyl containing 1 to 4 carbon atoms, cycloalkyl containing 3 to 8 carbon atoms, unsubstituted phenyl or phenyl which is substituted by 1 to 3 substituents on the phenyl ring selected from hydroxy and alkoxy containing 1 to 4 carbon atoms; or both of $R_3$ and $R_4$ are alkyl containing 1 to 4 carbon atoms.

More preferred are the compounds of formula [I] wherein $R_1$ is hydrogen atom or halogen atom; $R_2$ is unsubstituted phenyl, phenyl substituted by halogen atom, 2-pyridyl or 4-pyridyl; a is 2; Y is alkylene containing 3 to 10 carbon atoms; and one of $R_3$ and $R_4$ is hydrogen atom and the other is hydrogen atom, alkyl containing 1 to 4 carbon atoms, hydroxyalkyl containing 1 to 4 carbon atoms, cycloalkyl containing 3 to 6 carbon atoms or tri($C_1$–$C_4$ alkoxy)-substituted phenyl; or both of $R_3$ and $R_4$ are alkyl containing 1 to 4 carbon atoms.

Particularly preferred are the compounds of formula [I] wherein $R_1$ is meta- or para-halogen atom, particularly chlorine atom or fluorine atom; and $R_2$ is unsubstituted phenyl, 4-fluorophenyl, 2-pyridyl or 4-pyridyl. Further particularly preferred are the compound of formula [I] wherein $R_1$ is meta- or para-chlorine atom; and $R_2$ is unsubstituted phenyl, and the compound of the formula [I] wherein $R_1$ is para-fluorine atom; and $R_2$ is 2-pyridyl.

Pharmacologically acceptable salts of the compounds of the formula [I] include acid addition salts and alkali addition salts. The acid addition salts include inorganic acid salts such as hydrochloride, hydrobromide, hydroiodide, sulfate, nitrate, phosphate, etc. and organic salts such as acetate, oxalate, maleate, fumarate, lactate, malate, citrate, tartrate, benzoate, methanesulfonate, ethanesulfonate, benzenesulfonate, etc. The alkali addition salts include alkali metal or alkaline earth metal salts (e.g. sodium, potassium, calcium), ammonium salts, and salts of organic base such as methylamine, ethylamine, dimethylamine, triethylamine, ethanolamine, piperidine, etc.

When the compounds of the formula [I] have asymmetric carbon atoms, there exist optical isomers. And these stereoisomers and the mixture thereof are also included in the scope of the present invention.

Novel diazacycloalkanealkylsulfonamide derivatives of the formula [I] of the present invention may be prepared by various methods.

That is, the compounds of the formula [I] of the present invention may be prepared by a method as shown in the following reaction schemes A, B or C.

alcoholic solvents such as methanol, ethanol, isopropanol and n-butanol, aprotic polar solvents such as tetrahydrofuran, dioxane, acetone, acetonitrile, N,N-dimethylformamide, dimethylsulfoxide, chloroform, dichloromethane, tetrachloromethane, diethyl ether and diisopropyl ether, and aromatic hydrocarbon solvents such as benzene, toluene and xylene. The reactions are carried out at a temperature in the range of 0° C. to 200° C. Dehydrohalogenating agents include, for example, inorganic bases such as potassium carbonate, sodium carbonate, potassium hydrogencarbonate, sodium hydrogencarbonate and organic bases such as pyridine and triethylamine.

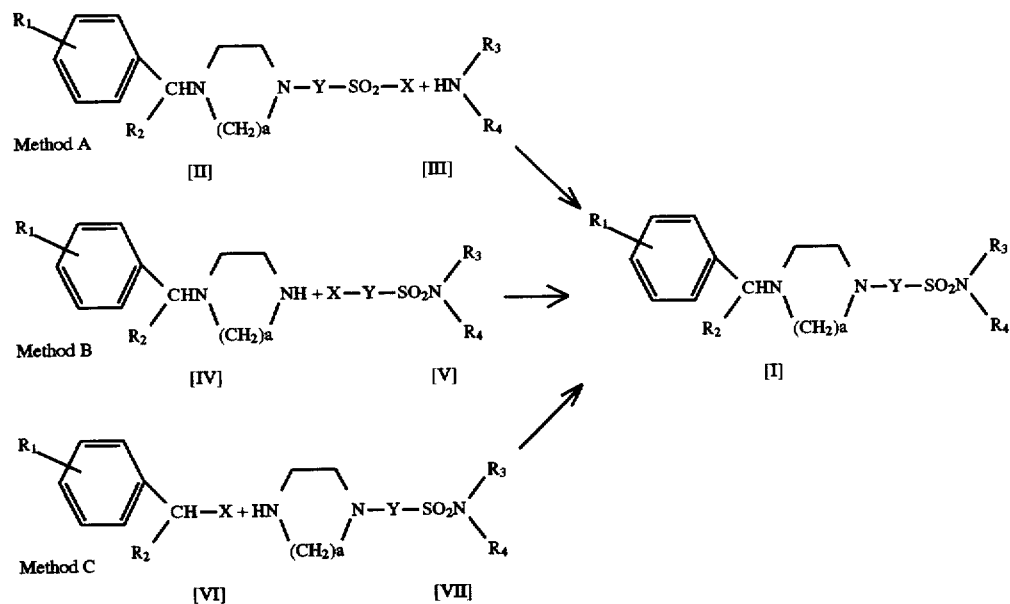

[wherein X refers to halogen (Cl, Br or I); $R_1$, $R_2$, $R_3$, $R_4$, a and Y are the same as defined above]

All of the methods A, B and C are conducted by subjecting each reactants to condensation reaction in the presence of a dehydrohalogenating agent in a suitable organic solvent. Any organic solvents which do not inhibit the condensation reaction may be used for the condensation and include The compounds of the formula [II] used as the starting material may be prepared by a method of the following reaction scheme.

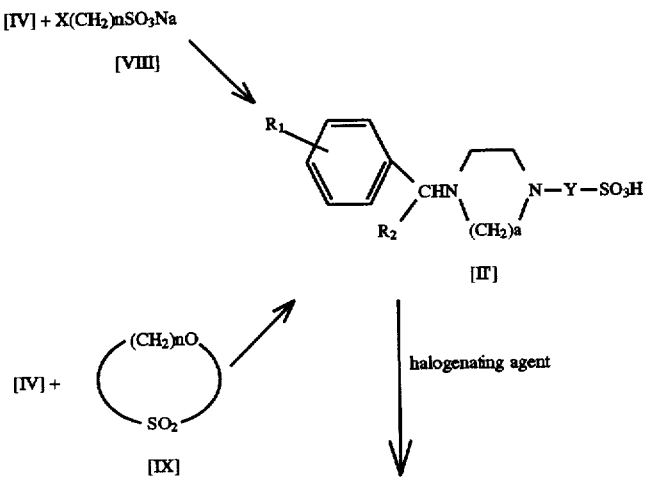

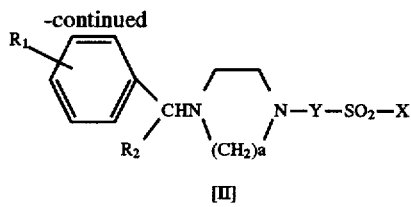

[wherein each groups are the same as defined above.]

In the above reaction scheme, a piperazine compound of the formula [IV] is reacted with sodium halogenoalkylsulfonate [VIII] [see, Organic Synthesis, collective Vol. 2, p558] in dry dimethylformamide at reflux temperature, or alternatively according to a method disclosed in Japanese Patent First Publication No. 233670/1990, the piperazine compound [IV] is reacted with cyclic sulfonic ester [IX] to give a sulfonic acid derivative [II']. Thus obtained compound [II'] is halogenated to give the compound [II]. This halogenation can readily be carried out by a conventional method using a thionyl halide or phosphorus halide as a halogenating agent. Thionyl halide such as thionyl chloride, thionyl bromide can be employed. The halogenation can be carried out by treating the sulfonic acid derivative [II'] with the thionyl compound in an excess amount of said thionyl compound or in an solvent such as benzene, toluene, xylene, dichloromethane, chloroform, dimethylformamide or diethyl ether at 0° to 200° C. for 30 minutes to 5 hours to give the compound [II], which reaction is carried out optionally after converting the sulfonic acid derivative to sodium sulfonate or in the presence of tertiary amine such as pyridine, quinoline, dimethylaniline, triethylamine and diisopropylethylamine. Phosphorus halides such as phosphorus trichloride, phosphorus pentachloride, phosphorus tribromide, phosphorus pentabromide and phosphorus oxychloride can be employed. The compound [II] can be obtained by using these phosphorus halides under the same conditions as in the reaction using thionyl halide as mentioned above.

The compounds of the formulae [IV] and [VI] (except a part) are disclosed, for example, in Journal of Pharmaceutical Science, Vol. 67, p900 (1978) and may be prepared by a method of the following reaction scheme.

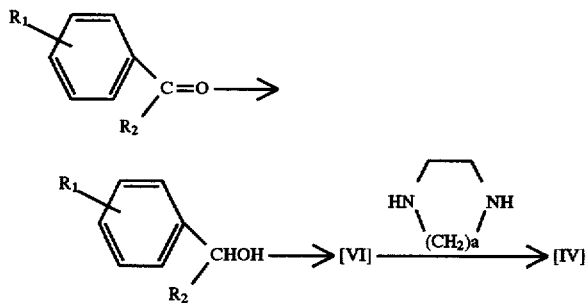

Pharmaceutical compositions comprising the novel diazacycloalkanealkylsulfonamide derivative of the formula [I] or a pharmaceutically acceptable salt thereof as an active ingredient may be administered by both of oral and parenteral routes.

The dosage forms for oral administration include tablets, capsules, powders, fine granules, granules, solutions, syrups, etc. The dosage form for parenteral administration include injections, suppositories, inhalants, eye drops, nasal drops, ointments, patches, etc. These preparations can be prepared with pharmaceutically acceptable additives such as excipients, disintegrators or disintegration auxiliaries, binders, lubricants, coating agents, pigments, diluents, bases, solvents or solubilizing agents, isotonicity agents, pH adjusters, stabilizers, propellants, adhesives.

The preparations for oral administration or for transdermal or mucosal administration are prepared by using excipients such as glucose, lactose, D-mannitol, starch and crystalline cellulose; disintegrators or disintegration auxiliaries such as carboxymethyl cellulose, starch and carboxymethyl cellulose calcium; binders such as hydroxypropyl cellulose, hydroxymethyl cellulose, polyvinyl pyrrolidone and gelatin; lubricants such as magnesium stearate and talc; coating agents such as hydroxypropylmethyl cellulose, sugars, polyethylene glycol and titanium oxide; bases such as petrolatum, liquid paraffin, polyethylene glycol, gelatin, kaolin, glycerin, purified water and hard fat; propellants such as furon, diethyl ether and compressed gas; adhesives such as sodium polyacrylate, polyvinyl alcohol, methyl cellulose, polyisobutylene and polybutene; and substrates such as cotton cloth or plastics sheet and the like.

The preparations for injection are prepared by using solvents or solubilizing agents suitable for preparing aqueous injections or injections to be dissolved when used, such as distilled water for injection, saline, propylene glycol; isotonicity agents such as glucose, sodium chloride, D-mannitol, glycerin; pH adjusters such as inorganic and organic acids; or inorganic and organic bases.

The dosage of a compound of formula [I] will vary depending on age of patients, severity of diseases, etc. Generally, the dose for oral administration is about 0.1 to 300 mg/day in adult.

Best mode for carrying out the invention

The compounds of this invention are illustrated by the following Experiments, Reference Examples and Examples, but should not be construed to be limited thereto.

Experiment 1

Activity of suppressing passive cutaneous anaphylaxis (PCA)

Test compounds were examined on their antiallergic activities. Male Wistar rats (weighing 150 to 200 g) were subjected to passive sensitization by intracutaneous injection of a monoclonal anti-DNP antibody to the bilateral regions on the back of the rats, said monoclonal anti-DNP antibody showing 1:1024 of 48 hours homologous PCA (passive cutaneous anaphylaxis) titer, which was diluted to 1000fold with saline and was injected in an amount of 0.1 ml. After 48 hours, 1.0 ml of 0.5 % Evans Blue saline solution containing DNP.BSA (1 mg in protein) was injected through the tail vein to induce allergic reaction. After 30 minutes, the rats were sacrificed by bleeding and the skin of back where dye was leaked out was flayed and put it into 20 ml test tube with ground stopper. Thereto was added 1.0 ml of 1N KOH aqueous solution and then it was allowed to stand at 37° C. in incubator overnight for lysing. To this solution was added 8.3 ml of a mixture of acetone and 0.6N phosphoric acid (13:5) and the mixture was mixed well and then was filtered to remove the insoluble materials. An amount of dye was determined by measuring the absorbance at 620 nm of the filtrate.

The test compounds were administered orally 1 hour before the antigen challenge. Suppression rate was expressed by percentage to the value in control where 0.5% aqueous methylcellulose solution was orally administered.

The results are shown in Table 1 below. As in shown therein, each compound showed PCA suppression activity of about 71 to 98% in a dosage of 10 mg/kg.

TABLE 1

| test compound Ex. No. | % suppression of rat PCA (10 mg/kg-po) | test compound Ex. No. | % suppression of rat PCA (10 mg/kg-po) |
|---|---|---|---|
| 3 | 95.2 | 101 | 88.0 |
| 4 | 89.0 | 104 | 86.7 |
| 13 | 73.8 | 106 | 90.3 |
| 19 | 78.0 | 107 | 87.8 |
| 21 | 89.7 | 108 | 82.2 |
| 26 | 71.0 | 110 | 88.3 |
| 29 | 95.7 | 113 | 87.5 |
| 31 | 87.2 | 114 | 83.5 |
| 32 | 86.8 | 115 | 73.2 |
| 34 | 84.8 | 116 | 70.2 |
| 36 | 77.5 | 120 | 93.4 |
| 39 | 83.8 | 123 | 83.5 |
| 42 | 80.2 | 124 | 88.4 |
| 43 | 86.5 | 126 | 80.8 |
| 45 | 84.0 | 127 | 90.7 |
| 48 | 83.8 | 128 | 86.1 |
| 54 | 89.2 | 129 | 92.2 |
| 56 | 94.5 | 134 | 87.1 |
| 57 | 90.6 | 135 | 74.4 |
| 58 | 76.5 | 136 | 80.2 |
| 59 | 96.4 | 137 | 75.8 |
| 61 | 89.7 | 141 | 87.4 |
| 64 | 72.5 | 143 | 87.8 |
| 65 | 74.7 | 149 | 97.7 |
| 66 | 82.8 | 150 | 89.1 |
| 67 | 84.1 | 153 | 86.2 |
| 68 | 94.5 | Ref. Ex. 4 | 0 |
| 69 | 88.3 | ketotifen, | 47.4–73.6 |
| 82 | 86.8 | | (2 mg/kg-po) |
| 99 | 72.1 | | |

Experiment 2

Antihistaminic activity

Female Hartley guinea pig (weighing 500 to 650 g) were sacrificed and the ileum (length of about 10 to 25 cm) was extracted from the ileocecum to prepare a specimen (length of 3 cm). The specimen was suspended with a load of 0.5 g in a Magnus tube filled with Tyrode (30°±1° C.) under flowing of a mixture of 95% $O_2$ gas+5% $CO_2$ gas. After allowing to stand for 60 minutes to make the specimen stable, a histamine ($3\times10^{-7}$M) was applied to the specimen at single application. Contraction of the specimen was determined and recorded using isotonic transducer. After repeating application of a histamine to make the contraction constant, a diluted solution of the test compound was applied. Three minutes after the application, a histamine was then added and an activity of suppressing contraction was examined. The results were shown by the molar concentration (M) of the test compound which effected 50% suppression of contraction ($EC_{50}$ value). The results are shown in Table 2. All compounds of the present invention had antihistaminic activity lower than that of ketotifen which was a reference compound.

TABLE 2

| test compound Ex. No. | anti-His in extracted ileum $EC_{50}$ (M) | test compound Ex. No | anti-His in extracted ileum $EC_{50}$ (M) |
|---|---|---|---|
| 3 | $7.6 \times 10^{-7}$ | 99 | $1.3 \times 10^{-6}$ |
| 4 | $6.5 \times 10^{-7}$ | 101 | $8.1 \times 10^{-7}$ |
| 13 | $3.2 \times 10^{-7}$ | 104 | $6.8 \times 10^{-6}$ |
| 19 | $4.6 \times 10^{-7}$ | 106 | $4.0 \times 10^{-7}$ |
| 21 | $5.1 \times 10^{-7}$ | 107 | $6.2 \times 10^{-7}$ |
| 26 | $3.0 \times 10^{-7}$ | 108 | $6.8 \times 10^{-7}$ |
| 29 | $7.5 \times 10^{-7}$ | 110 | $5.7 \times 10^{-7}$ |
| 31 | $7.7 \times 10^{-7}$ | 113 | $7.1 \times 10^{-7}$ |
| 32 | $8.4 \times 10^{-7}$ | 114 | $5.6 \times 10^{-7}$ |
| 34 | $3.3 \times 10^{-7}$ | 115 | $7.9 \times 10^{-7}$ |
| 36 | $5.6 \times 10^{-7}$ | 116 | $1.2 \times 10^{-7}$ |
| 39 | $8.1 \times 10^{-7}$ | 120 | $7.0 \times 10^{-7}$ |
| 42 | $3.3 \times 10^{-7}$ | 123 | $3.3 \times 10^{-7}$ |
| 43 | $6.9 \times 10^{-7}$ | 124 | $2.0 \times 10^{-7}$ |
| 45 | $7.4 \times 10^{-7}$ | 126 | $3.0 \times 10^{-7}$ |
| 48 | $3.5 \times 10^{-7}$ | 127 | $4.1 \times 10^{-7}$ |
| 54 | $4.2 \times 10^{-7}$ | 128 | $3.2 \times 10^{-7}$ |
| 56 | $4.4 \times 10^{-7}$ | 129 | $1.8 \times 10^{-6}$ |
| 57 | $3.9 \times 10^{-7}$ | 134 | $5.8 \times 10^{-7}$ |
| 58 | $3.5 \times 10^{-7}$ | 135 | $1.1 \times 10^{-6}$ |
| 59 | $2.9 \times 10^{-6}$ | 136 | $5.4 \times 10^{-7}$ |
| 61 | $3.1 \times 10^{-7}$ | 137 | $2.2 \times 10^{-6}$ |
| 64 | $3.6 \times 10^{-7}$ | 141 | $2.1 \times 10^{-7}$ |
| 65 | $4.3 \times 10^{-7}$ | 143 | $2.8 \times 10^{-6}$ |
| 66 | $4.2 \times 10^{-7}$ | 149 | $3.1 \times 10^{-7}$ |
| 67 | $4.2 \times 10^{-7}$ | 150 | $3.5 \times 10^{-7}$ |
| 68 | $3.7 \times 10^{-7}$ | 153 | $2.6 \times 10^{-6}$ |
| 69 | $1.5 \times 10^{-7}$ | ketotifen | $4.0$–$5.5 \times 10^{-9}$ |
| 82 | $7.9 \times 10^{-7}$ | | |

Experiment 3

Toxicity Test

The test compounds were orally administered to male ICR mice (weighing to 30 g) after fasting overnight. The life or death of these mice was observed for 24 hours. The results were expressed by minimum lethal dose. The results were shown in Table 3. Toxicity of any compounds of the present invention were weaker than that of ketotifen which was a reference compound.

TABLE 3

| test compound Ex. No. | mouse acute toxicity (lethal dose) (10 mg/kg-po) | test compound Ex. No. | mouse acute toxicity (lethal dose) (10 mg/kg-po) |
|---|---|---|---|
| 3 | >500 | 66 | >500 |
| 4 | >500 | 67 | >500 |
| 13 | >500 | 69 | >500 |
| 21 | >500 | 99 | >500 |
| 26 | >500 | 101 | >500 |
| 29 | >500 | 104 | >500 |
| 31 | >500 | 108 | >500 |
| 32 | >500 | 115 | >500 |
| 39 | >500 | 116 | >500 |
| 42 | >500 | 120 | >500 |
| 43 | >500 | 124 | >500 |
| 45 | >500 | 128 | >500 |
| 48 | >500 | 129 | >500 |
| 54 | >500 | 135 | >500 |
| 56 | >500 | 136 | >500 |
| 59 | >500 | 137 | >500 |
| 61 | >500 | 143 | >500 |

TABLE 3-continued

| test compound | mouse acute toxicity (lethal dose) (10 mg/kg-po) | test compound | mouse acute toxicity (lethal dose) (10 mg/kg-po) |
|---|---|---|---|
| 64 | >500 | 150 | >500 |
| 65 | >500 | 153 | >500 |
|  |  | ketotifen | 500 |

Experiment 4
Mouse Biphasic Allergic Dermal Reaction

Female Balb/c mice (weighing 18 to 25 g) were subjected to passive sensitization by intravenous administration of 1 ml of anti-DNP monoclonal IgE antibody showing 1:1024 of antibody titer. 24 hours after the sensitization, 25 μl of 0.15% dinitrofluorobenzene (DNFB) were applied to both sides of right and left auricles of mouse for inducing allergic reactions. Thickness of auricles were measured using Dial Thickness Gauge before the challenge with DNFB, and 1 and 24 hours after the challenge. And then, increase in thickness of auricles at 1 hour after the challenge (edema caused by immediate allergic reaction) and that at 24 hours after the challenge (edema caused by late allergic reaction) were calculated against the thickness of auricles before the challenge with DNFB, respectively.

Suppression rate was expressed by relative ratio (%) to the value in control in which a solvent was administered.

Test compounds, diphenhydramine which is a existing classical antihistamic drug, amlexanox which is an antiallergic drug and dexamethasone which is a steroidal drug were administered orally (partly intraperitoneally) once before antigen challenge. The results were shown in Table 4.

The above test was performed by using a mouse biphasic allergic dermal reaction model which was a new model [see, Sakurai T, Inagaki, N. and Nagai, H Life Sci., 54, PL291-295 (1994)]. In this model, the immediate allergic reaction was induced by mediator release from mast cell at 1 hour after the challenge, and the late allergic reaction with inflammatory cells such as eosinophil (edema after 24 hours) was induced after 24 hours from the challenge.

TABLE 4

| | | mouse biphasic allergic dermal reaction | |
|---|---|---|---|
| test compound | dose mg/kg | immediate edema (1 hr) suppression (%) | late edema (24 hr) suppression (%) |
| Example 54 | 0.1 | 19.0 | 37.0 |
|  | 1.0 | 52.4 | 51.9 |
| Example 56 | 0.1 | NE | 3.8 |
|  | 1.0 | 15.8 | 34.6 |
| Example 57 | 0.1 | NE | 7.7 |
|  | 1.0 | 31.6 | 46.2 |
| Example 61 | 0.1 | 5.0 | 37.0 |
|  | 1.0 | NE | 44.4 |
| Example 120 | 0.1 | 26.1 | 7.1 |
|  | 1.0 | 56.5 | 25.0 |
| Example 128 | 0.1 | 32.0 | 36.0 |
|  | 1.0 | 28.0 | 40.0 |
| Example 143 | 0.1 | 24.0 | 4.0 |
|  | 1.0 | 40.0 | 28.0 |
| Example 153 | 0.1 | 24.0 | 24.0 |
|  | 1.0 | 56.0 | 48.0 |
| diphenhydramine | 3.0 | 17.8 | NE |
|  | 10.0 | 13.3 | NE |
|  | 30.0 | 53.30 | 14.3 |

TABLE 4-continued

| | | mouse biphasic allergic dermal reaction | |
|---|---|---|---|
| test compound | dose mg/kg | immediate edema (1 hr) suppression (%) | late edema (24 hr) suppression (%) |
| amlexanox | 3.0 | 38.5 | 12.1 |
|  | 10.0 | 38.5 | NE |
|  | 30.0 | 50.0 | 6.1 |
| dexamethasone | 0.1 (i.p.) | 32.4 | 34.3 |
|  | 1.0 | 32.4 | 42.9 |
|  | 3.0 | 11.8 | 45.7 |

NE : non-effect

As shown in the above results, diphenhydramine which is a classical antihistamic drug and amlexanox which is a typical mediator release inhibitor suppressed the immediate allergic reaction (edema after 1 hour), but did not suppress the late allergic reaction (edema after 24 hours). On the other hand, the test compounds of Example 54, 56, 57, 61, 120, 128, 143 and 153 showed strong activity of suppressing the late allergic reaction. In addition, dexamethasone which is a steroidal drug also showed the strong activity of suppressing the late allergic reaction.

As shown in the above pharmacological tests, it was found that the compounds of the present invention had strong activity of suppressing PCA and showed obviously weaker antihistaminic activity indicated by activity of suppressing contraction of extracted ileum of guinea pig than the reference compound. Further, as shown in the above toxicity test, any test compounds showed weaker toxicity than the reference compound and therefore they have very high safety. Accordingly, the compounds of the present invention are useful clinically as a medicament and can be continuously administered for a long period of time. And further, as they have activity of suppressing the late allergic reaction, they are useful as a medicament for treating allergic disease, particularly bronchial asthma and atopic dermatitis.

REFERENCE EXAMPLE 1

Preparation of sodium 6-bromohexylsulfonate

To a stirred mixture of dibromohexane (81.0 g), ethanol (120 ml) and water (50 ml) is added dropwise an aqueous solution (50 ml) of sodium sulfite (12.5 g) under reflux over 2 hours. After additional refluxing for 2 hours, the reaction mixture is allowed to cool and unreacted dibromohexane is removed and then the resulting solution is concentrated under reduced pressure. 95% Ethanol (200 ml) is added and the mixture is allowed to cool at room temperature overnight and precipitated crystals are collected by filtration to give the title compound as colorless prisms. The filtrate is concentrated and is allowed to cool overnight and precipitated crystals are collected by filtration to give additional title compound.

First crystals: yield 11.1 g (41.5%), mp.>300° C.

Second crystals: yield 7.0 g (26.2%), mp.>300° C.

REFERENCE EXAMPLE 2

Preparation of (2-fluorophenyl)phenylmethanol and [(2-fluorophenyl)phenylmethyl]piperazine:

2-Fluorobenzophenone (15.0 g) is dissolved in ethanol and sodium borohydride (3.8 g) is added in portions and the mixture is stirred for 20 hours. The reacted solution is concentrated under reduced pressure and extracted with chloroform and water to give crude (2-fluorophenyl) phenylmethanol (15.0 g) (quantitative) as colorless liquid.

Then, the crude product (15.0 g) is dissolved in methylene chloride (100 ml), a solution of thionyl chloride (25.0 g) in methylene chloride is added dropwise under ice cooling and the mixture is refluxed for 3 hours. The reacted solution is concentrated under reduced pressure, added dropwise into a solution of piperazine (27.5 g) in isopropanol and refluxed for 24 hours. After concentrating under reduced pressure, the solution is extracted with chloroform and water to give [(2-fluorophenyl)phenylmethyl]piperazine (17.5 g, 87%) as pale yellow liquid.

REFERENCE EXAMPLE 3

Preparation of 6-[[4-(2-fluorophenyl)phenylmethyl]-1-piperazinyl]hexylsulfonic acid:

[(2-Fluorophenyl)phenylmethyl]piperazine (2.0 g), sodium 6-bromohexylsulfonate (5.9 g) and dry dimethylformamide (150 ml) are added to a flask and the mixture is heated and stirred at 180° C. for 16 hours. The solution is concentrated under reduced pressure and recrystallized from ethanol-acetone to give the title compound (2.0 g, 64%) as colorless prisms. mp. 261°–262° C.

REFERENCE EXAMPLE 4

Preparation of 4-[4-[4-fluorophenyl-(2-pyridyl)methyl]-1-piperazinyl]butylsulfonic acid:

After a mixture of [4-fluorophenyl-(2-pyridyl)methyl] piperazine (2.71 g), 1,4-butanesultone (4.08 g) and isobutylmethylketone (60 ml) is heated at reflux temperature for 20 hours, precipitated crystals are collected by filtration and recrystallized from ethanol-acetone to give the title compound (2.91 g, 71.5%). mp. 231°–232° C.

REFERENCE EXAMPLE 5

Preparation of 6-piperazinylhexylsulfonedimethylamine:

1-Benzylpiperazine (3.5 g), sodium 6-bromohexylsulfonate (16.2 g) and dry dimethylformamide (150 ml) are added to a flask and the mixture is heated and stirred at 180° C. for 16 hours. Precipitated crystals are collected by filtration and recrystallized from ethanol-diethyl ether to give 6-(4-benzyl-1-piperazinyl) hexylsulfonic acid (4.36 g, 63.5%) as colorless prisms. mp. 228°–230° C.

To the above sodium salt (4.0 g) is added thionyl chloride (20 ml) under ice cooling and stirred, and then, heated at 50° C. for 30 minutes. After distilling off unreacted thionyl chloride, a solution of dimethylamine in acetonitrile (10% w/w, 20 ml) is added dropwise under ice cooling and stirred at room temperature for 3 hours. After filtering off insoluble materials, the solvent is distilled off to give a brown liquid. The liquid is treated by column chromatography [silica gel, chloroform-methanol (100:2)] and the resulting purified material (1.8 g) is dissolved in ethanol and the solution is subjected to catalytic reduction by adding 10% palladium/carbon (1.5 g). The resulting brown liquid is treated by column chromatography [silica gel, chloroform-methanol (100:1)] to give the title compound (1.08 g, 80%) as pale yellow liquid.

EXAMPLE 1

(Method A)

Preparation of 10-[4-(diphenylmethyl)-1-piperazinyl] decanylsulfonamide hydrochloride:

Sodium 10-[4-(diphenylmethyl)-1-piperazinyl] decanylsulfonate (1.0 g) is added to thionyl chloride (10 ml) under ice cooling and the mixture is stirred and then heated at 50° C. for 30 minutes. After distilling off unreacted thionyl chloride, a solution of ammonia in acetonitrile (5% w/w, 20 ml) is added dropwise under ice cooling and stirred at room temperature for 3 hours. After filtering off insoluble materials, the solvent is distilled off to give a brown liquid. The liquid is treated by column chromatography [silica gel, chloroform-methanol (20:1)] and the resulting purified material (0.83 g, 77.7%) is converted into hydrochloride by using hydrochloric acid-methanol solution and recrystallized from ethanol-diethyl ether to give the title compound as pale yellow crystals. mp.125°–130° C.

Mass Spectrum (MS): m/z:471 (M⁺);

NMR Spectrum: δ(CDCl₃) ppm: 1.10–2.20 (16H,m), 2.35–2.95 (10H, m), 2.96–3.40 (2H, m), 4.32 (1 H, s), 5.35 (2H, s), 7.18–7.68 (10H, m).

EXAMPLES 2 TO 17

Compounds of Table 5 below are prepared from various starting materials according to the same manner as described in Example 1.

TABLE 5

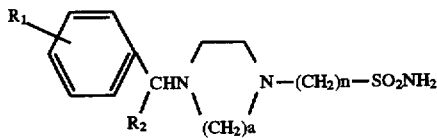

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 2 | H | ⌬ | 2 | 8 | pale brown crystals | 135–140 | 443 | 1.16–2.10(16H, m), 2.10–2.86(10H, m), 2.92–3.29(2H, m), 4.27(1H, s), 4.54(2H, s), 7.06–7.77(10H, m) |

TABLE 5-continued

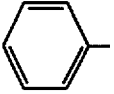

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 3 | 4-Cl | phenyl | 2 | 6 | colorless crystals | 112–116 | 449 | 1.12–2.08(8H, m), 2.43–3.53(12H, m)4.28(1H, s), 5.25 (2H, s)7.01–7.42(9H, m) |
| 4 | 4-Cl | phenyl | 2 | 8 | colorless crystals | 105–109 | 477 | 1.02–2.04(12H, m), 2.09–2.68(10H, m)2.79–3.22(2H, m), 4.17(1H, s)4.40(2H, b), 6.99–7.47(9H, m) |
| 5 | 4-Cl | 4-Cl-phenyl | 2 | 8 | colorless crystals | 153–155 | 511 | 1.07–2.01(12H, m), 2.21–2.87(10H, m)2.89–3.32(2H, m), 4.20(1H, s)4.43(2H, b), 7.04–7.48(8H, m) |
| 6 | 4-F | pyridyl | 2 | 8 | pale brown crystals | 152–156 | 462 | 1.03–2.01(12H, m), 2.05–2.78(10H, m)2.80–3.25(2H, m), 4.21(1H, s)4.31–5.01(2H, b), 6.62–8.55(8H, m) |
| 7 | 4-F | pyridyl | 2 | 2 | pale yellow crystals | 225–230 | 378 | 2.25–2.70(8H, m), 2.80–3.35(4H, m)4.38(1H, s), 6.75–8.50(8H, m) |
| 8 | 4-F | pyridyl | 2 | 3 | colorless crystals | 135–140 | 392 | 1.77–2.81(12H, m), 3.17(2H, t)4.39(1H, s), 4.69(2H, b) 6.75–8.43(8H, m) |
| 9 | 4-F | pyridyl | 2 | 4 | pale yellow crystals | 225–230 | 406 | 1.40–2.20(4H, m), 2.20–3.90(12H, m)4.48(1H, s), 5.20–5.90(2H, b)6.60–8.36(8H, m) |
| 10 | 4-F | pyridyl | 2 | 5 | colorless crystals | 165–170 | 420 | 1.10–2.00(6H, m), 2.10–2.70(10H, m)2.85–3.25(2H, m), 4.00–4.70(2H, b)4.34(1H, s), 6.70–8.56(8H, m) |
| 11 | 4-F | pyridyl | 2 | 6 | pale brown crystals | 150–155 | 434 | 1.08–2.09(8H, m), 2.10–2.74(10H, m)3.09(2H, t), 4.41(1H, s)4.79(2H, b), 6.60–8.66(8H, m) |
| 12 | 4-F | pyridyl | 2 | 7 | colorless crystals | 155–160 | 448 | 1.10–2.00(10H, m), 2.00–2.70(10H, m)2.92–3.27(2H, m), 4.00–4.70(2H, b)4.37(1H, s), 6.70–8.43(8H, m) |
| 13 | 4-F | pyridyl | 2 | 8 | pale brown crystals | 140–150 | 462 | 1.03–2.15(12H, m), 2.18–2.83(10H, m)3.08(2H, t), 4.08–4.88(2H, b)4.37(1H, s), 6.68–8.43(8H, m) |
| 14 | 4-F | pyridyl | 2 | 9 | pale brown crystals | 141–145 | 476 | 1.10–2.10(14H, m), 2.12–2.80(10H, m)2.98–3.32(2H, m), 4.47(1H, s)6.70–8.70(8H, m) |

TABLE 5-continued $$R_1\text{-}C_6H_4\text{-}CH(R_2)\text{-}NH\text{-}N[(CH_2)_a]\text{-}N\text{-}(CH_2)_n\text{-}SO_2NH_2$$

| Ex. No. | $R_1$ | $R_2$ | a | n | aspect | m p. (°C.) | MS (M/Z)M+ | NMR δ (CDCl₃) ppm |
|---|---|---|---|---|---|---|---|---|
| 15 | 4-F | pyridyl | 2 | 10 | pale yellow crystals | 107–112 | 490 | 1.02–2.02(16H, m), 2.07–2.80(10H, m)2.90–3.34(2H, m), 4.44(1H, s)4.70–5.30(2H, b), 6.42–8.60(8H, m) |
| 16 | 4-F | pyridyl | 2 | 11 | pale brown crystals | 79–83 | 504 | 1.05–2.12(18H, m), 2.20–2.96(10H, m)2.97–3.38(2H, m), 4.45(1H, s)5.02(2H, b), 6.70–8.70(8H, m) |
| 17 | 4-F | pyridyl | 2 | 12 | pale yellow crystals | 114–118 | 518 | 1.07–2.05(20H, m), 2.07–2.80(10H, m)3.15(2H, t), 4.00–4.85(2H, b), 4.44(1H, s), 6.80–8.65(8H, m) |

EXAMPLES 18 TO 28

Compounds of Table 6 below are prepared from various starting materials according to the same manner as described in Example 1 except using methylamine instead of ammonia.

TABLE 6

$$R_1\text{-}C_6H_4\text{-}CH(R_2)\text{-}NH\text{-}N[(CH_2)_a]\text{-}N\text{-}(CH_2)_n\text{-}SO_2NHCH_3$$

| Ex. No. | $R_1$ | $R_2$ | a | n | aspect | m p. (°C.) | MS (M/Z)M+ | NMR δ (CDCl₃) ppm |
|---|---|---|---|---|---|---|---|---|
| 18 | H | phenyl | 2 | 3 | pale yellow crystals | 120–125 | 387 | 1.07–2.20(2H, m), 2.20–2.84(10H, m)2.68(3H, s), 3.04(2H, t), 4.25(1H, s)5.20–5.77(1H, b), 6.98–7.61(10H, m) |
| 19 | H | phenyl | 2 | 5 | pale yellow crystals | 128–133 | 415 | 1.10–2.10(6H, m), 2.10–2.66(10H, m)2.69–3.24(5H, m), 4.23(1H, s)4.30–4.70(1H, b), 7.10–7.60(10H, m) |
| 20 | H | phenyl | 2 | 6 | pale yellow crystals | 190–192 | 429 | 1.20–2.05(8H, m), 2.15–2.61(10H, m)2.69–3.20(5H, m), 4.22(1H, s)4.40–4.70(1H, b), 7.10–7.70(10H, m) |
| 21 | 4-Cl | phenyl | 2 | 6 | pale orange crystals | 169–174 | 463 | 1.11–2.04(8H, m), 2.08–2.62(10H, m)2.63–3.13(5H, m), 4.16(1H, s)4.47(1H, b), 6.98–7.46(9H, m) |
| 22 | 4-F | pyridyl | 2 | 2 | colorless crystals | 165–170 | 392 | 1.85–3.37(15H, m), 4.43(1H, s)4.82–5.35(1H, b), 6.74–8.80(8H, m) |

TABLE 6-continued

R₁-C₆H₄-CH(R₂)-NH-[piperidine/pyrrolidine ring with (CH₂)a]-N-(CH₂)n-SO₂NHCH₃

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 23 | 4-F | pyridyl | 2 | 3 | pale yellow crystals | 145–150 | 406 | 1.62–2.20(2H, m), 2.28–2.64(10H, m)2.71(3H, s), 3.04(2H, t), 4.39(1H, s)5.12–5.72(1H, b), 6.74–8.52(8H, m) |
| 24 | 4-F | pyridyl | 2 | 4 | yellow crystals | 135–140 | 420 | 1.12–2.04(4H, m), 2.17–2.63(10H, m), 2.79(3H, s), 2.88–3.41(2H, m), 4.45(1H, s), 4.52–5.07(1H, b), 6.77–8.67(8H, m) |
| 25 | 4-F | pyridyl | 2 | 5 | pale yellow crystals | 140–145 | 434 | 1.12–2.10(6H, m), 2.10–2.65(10H, m), 2.78(3H, s), 2.78–3.28(2H, m), 4.43(1H, s), 4.50–4.90(1H, b), 6.68–8.63(8H, m) |
| 26 | 4-F | pyridyl | 2 | 6 | yellow crystals | 105–110 | 448 | 1.10–2.09(8H, m), 2.10–2.64(10H, m), 2.76(3H, s), 2.65–3.19(2H, m), 4.40(1H, s), 4.49(1H, b), 6.76–8.55(8H, m) |
| 27 | 4-F | pyridyl | 2 | 7 | yellow crystals | 135–140 | 462 | 1.04–2.07(10H, m)2.07–2.68(10H, m), 2.82(3H, s), 2.70–3.20(2H, m), 4.42(1H, s), 4.28–4.85(1H, b), 6.70–8.62(8H, m) |
| 28 | 4-F | pyridyl | 2 | 8 | yellow crystals | 122–127 | 476 | 1.07–2.13(12H, m)2.13–2.67(10H, m)2.67–3.27(5H, m), 4.40–4.77(1H, b)4.45(1H, s), 6.77–8.62(8H, m) |

EXAMPLES 29 TO 35

Compounds of Table 7 below are prepared from various starting materials according to the same manner as described in Example 1 except using ethylamine instead of ammonia.

TABLE 7

R₁-C₆H₄-CH(R₂)-NH-[ring with (CH₂)a]-N-(CH₂)n-SO₂NHC₂H₅

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 29 | 4-Cl | phenyl | 2 | 6 | pale brown crystals | 185–190 | 477 | 1.19(3H, t)1.16–2.06(8H, m)2.09–2.73(10H, m)2.77–3.18 (2H, m)3.07(2H, q)4.17(1H, s)4.22(1H, b), 7.04–7.45(9H, m) |
| 30 | 4-F | pyridyl | 2 | 3 | yellow crystals | 129–134 | 420 | 1.20(3H, t)1.67–2.27(2H, m)2.27–2.84(10H, m), 2.84–3.47 (4H, m), 4.47(1H, s)4.49–5.54(1H, b), 6.79–8.77(8H, m) |

TABLE 7-continued

Structure: R₁-phenyl-CH(R₂)-NH-[piperidine/ring with (CH₂)a]-N-(CH₂)n-SO₂NHC₂H₅

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 31 | 4-F | 2-pyridyl | 2 | 5 | pale yellow crystals | 115–120 | 448 | 1.21(3H, t)1.07–2.19(6H, m)2.20–2.80(10H, m), 2.80–3.39(4H, m), 4.45(1H, s)4.20–4.75(1H, b), 6.77–8.60(8H, m) |
| 32 | 4-F | 2-pyridyl | 2 | 6 | yellowish red crystals | 128–133 | 462 | 1.05–2.00(8H, b)1.20(3H, t)2.00–2.75(10H, m), 2.80–3.43(4H, m), 4.47(1H, s)4.15–4.55(1H, b), 6.80–8.68(8H, m) |
| 33 | 4-F | 2-pyridyl | 2 | 7 | yellow crystals | 88–92 | 476 | 1.02–2.07(10H, b)1.18(3H, t)2.07–2.71(10H, m)2.71–3.82(4H, m), 4.39(1H, s)4.50–4.94(1H, b), 6.78–8.52(8H, m) |
| 34 | 4-F | 2-pyridyl | 2 | 8 | pale brown crystals | 153–159 | 490 | 1.13–2.07(12H, b)1.21(3H, t)2.50–3.32(14H, m), 4.49(1H, s)4.70(1H, b), 6.79–8.51(8H, m) |
| 35 | 4-F | 2-pyridyl | 2 | 10 | brown crystals | 131–136 | 518 | 1.28–2.10(19H, m)2.10–2.79(10H, m), 2.79–3.40(4H, m), 4.22–4.65(1H, b)4.41(1H, s), 6.70–8.65(8H, m) |

EXAMPLES 36 TO 42

Compounds of Table 8 below are prepared from various starting materials according to the same manner as described in Example 1 except using propylamine instead of ammonia.

TABLE 8

Structure: R₁-phenyl-CH(R₂)-NH-[piperidine ring with (CH₂)a]-N-(CH₂)n-SO₂NHC₃H₇-(n)

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 36 | 4-Cl | phenyl | 2 | 6 | colorless crystals | 99–103 | 491 | 0.94(3H, t)1.27–2.20(10H, m)2.24–2.79(10H, m)2.74–3.17(2H, m), 3.09(2H, t)4.18(1H, s)4.38(1H, b), 7.00–7.53(9H, m) |
| 37 | 4-F | 2-pyridyl | 2 | 3 | pale yellow crystals | 130–135 | 434 | 0.92(3H, t)1.15–2.25(4H, m), 2.24–2.75(10H, m)2.75–3.30(4H, m), 4.42(1H, s)4.88–5.32(1H, b), 6.82–8.64(8H, m) |
| 38 | 4-F | 2-pyridyl | 2 | 5 | pale yellow crystals | 114–119 | 462 | 0.90(3H, t)1.10–2.15(8H, m), 2.15–2.75(10H, m)2.75–3.40(4H, m), 4.42(1H, s)4.55–4.95(1H, b), 6.70–8.65(8H, m) |

TABLE 8-continued

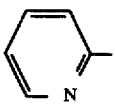

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 39 | 4-F | pyridyl | 2 | 6 | yellow crystals | 122–126 | 476 | 0.94(3H, t)1.19–2.12(10H, m), 2.15–2.75(10H, m)2.76–3.39(4H, m)4.43(2H, b)6.70–8.53(8H, m) |
| 40 | 4-F | pyridyl | 2 | 7 | brown crystals | 112–117 | 490 | 0.91(3H, t)1.10–2.08(12H, m), 2.18–2.70(10H, m)2.73–3.53(4H, m)4.36(1H, s)4.52–5.01(1H, b), 6.69–8.34(8H, m) |
| 41 | 4-F | pyridyl | 2 | 8 | yellow crystals | 118–122 | 504 | 0.97(3H, t)1.16–2.12(14H, m), 2.12–2.72(10H, m)2.73–3.48(4H, m)4.42(1H, s)4.00–4.68(1H, b), 6.48–8.54(8H, m) |
| 42 | 4-F | pyridyl | 2 | 10 | brown crystals | 111–115 | 532 | 0.80–2.08(21H, m), 2.14–2.77(10H, m), 2.79–3.48(4H, m), 4.44(1H, s), 4.56(1H, b), 6.86–8.52(8H, m) |

EXAMPLES 43 TO 49

Compounds of Table 9 below are prepared from various starting materials according to the same manner as described in Example 1 except using isopropylamine instead of ammonia.

TABLE 9

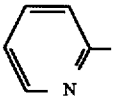

| Ex. No. | R₁ | R₂ | a | n | aspect | m.p. (°C.) | MS (M/Z)M⁺ | NMR δ(CDCl₃) ppm |
|---|---|---|---|---|---|---|---|---|
| 43 | 4-Cl | phenyl | 2 | 6 | pale yellow crystals | 105–110 | 491 | 1.20(6H, d), 1.12–2.03(8H, m), 2.08–2.67(10H, m), 2.77–3.11(2H, m), 3.59(1H, q), 4.21(1H, s), 6.97–7.40(9H, m) |
| 44 | 4-F | pyridyl | 2 | 3 | pale yellow crystals | 137–142 | 434 | 1.21(6H, d)1.66–2.26(2H, m) 2.26–2.76(10H, m)3.10(2H, t), 3.66(1H, q)4.46(1H, s)4.60–4.96(1H, b)6.82–8.66(8H, m; |
| 45 | " | " | 2 | 5 | yellow crystals | 119–124 | 462 | 1.11–2.13(12H, m), 2.15–2.76(10H, m) 2.88–3.25(2H, m), 3.74(1H, s)4.17(1H, b)4.97(1H, s), 6.86–8.63(8H, m) |
| 46 | " | " | 2 | 6 | yellow crystals | 127–132 | 476 | 1.22(6H, d)1.06–2.11(8H, m)2.17–2.78(10H, m)2.79–3.19(2H, m)3.67(1H, s)4.19(1H, b)4.43(1H, s))6.67–8.53(8H, m |
| 47 | " | " | 2 | 7 | yellow crystals | 89–94 | 490 | 1.07–2.10(10H, m), 1.22(6H, d)2.10–2.70(10H, m)3.57(1H, s)4.16(1H, b)4.43(1H, s), 6.77–8.51(8H, m) |
| 48 | " | " | 2 | 8 | yellow crystals | 128–133 | 504 | 1.18–2.05(18H, m), 2.12–2.71(10H, m) 2.83–3.18(2H, m)3.68(1H, q)4.19(1H, b), 4.42(1H, s), 6.80–8.53(8H, m) |

TABLE 9-continued

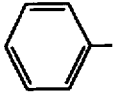

| Ex. No. | R₁ | R₂ | a | n | aspect | m.p. (°C.) | MS (M/Z)M⁺ | NMR δ(CDCl₃) ppm |
|---|---|---|---|---|---|---|---|---|
| 49 | " | " | 2 | 10 | pale yellow | 122–127 | 532 | 0.88–2.09(22H, m), 2.11–2.80(10H, m) 2.83–3.23(2H, m)3.56(1H, q)4.09(1H, b), 4.42(1H, s), 6.70–8.52(8H, m) |

EXAMPLES 50 TO 53

Compounds of Table 10 below are prepared from various starting materials according to the same manner as described in Example 1 except using tert-butylamine instead of ammonia.

TABLE 10

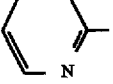

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 50 | 4-Cl | 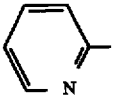 | 2 | 6 | pale yellow crystals | 128–132 | 505 | 1.04–2.26(17H, m), 2.43–3.53(12H, m)4.34(1H, s), 6.23 (1H, s)7.05–7.50(9H, m) |
| 51 | 4-F | 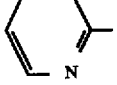 | 2 | 6 | brown crystals | 146–149 | 490 | 1.07–2.16(17H, m), 2.17–2.76(8H, m)2.80–3.26(4H, b), 4.35(1H, s)4.42(1H, s), 6.66–8.57(8H, m) |
| 52 | 4-F | 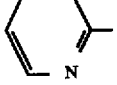 | 2 | 8 | yellow crystals | 107–111 | 518 | 1.11–2.14(12H, m), 1.37(9H, s), 2.15–2.69(8H, m), 2.70–3.24(4H, m), 4.23(1H, b), 4.43(1H, s), 6.79–8.63(8H, m) |
| 53 | 4-F | 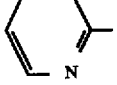 | 2 | 10 | pale yellow crystals | 119–123 | 546 | 1.06–2.21(25H, m), 2.43–3.63(12H, m)4.52(1H, s), 6.69–8.69(8H, m) |

EXAMPLES 54 TO 58

Compounds of Table 11 below are prepared from various starting materials according to the same manner as described in Example 1 except using cyclopropylamine instead of ammonia.

TABLE 11

$$R_1-\text{C}_6H_4-\text{CHR}_2-\text{NH}-\text{[piperazine ring with (CH}_2\text{)}_a\text{]}-N-(CH_2)_n-SO_2NH-\text{cyclopropyl}$$

| Ex. No. | $R_1$ | $R_2$ | a | n | aspect | m.p. (°C.) | MS (M/Z)M⁺ | NMR δ (CDCl₃) ppm |
|---|---|---|---|---|---|---|---|---|
| 54 | 4-Cl | phenyl | 2 | 6 | pale yellow crystals | 140–144 | 490 | 0.68(4H, d), 1.15–2.13(8H, m), 2.27–3.33(13H, m)4.26 (1H, s)5.70(1H, b), 7.07–7.46(9H, m) |
| 55 | 4-F | 2-pyridyl | 2 | 4 | pale brown crystals | 125–129 | 446 | 0.66(4H, d), 1.38–2.13(4H, m), 2.15–2.75(11H, m), 2.83–3.24(2H, m), 4.32(1H, s), 4.98(1H, b), 6.66–8.32(8H, m) |
| 56 | 4-F | 2-pyridyl | 2 | 6 | yellow crystals | 107–112 | 474 | 0.67(4H, d), 1.20–2.08(8H, m), 2.09–2.78(11H, m), 2.86–3.28(2H, m), 4.34(1H, s), 4.91(1H, b), 6.73–8.46(8H, m) |
| 57 | 4-F | 2-pyridyl | 2 | 8 | yellow crystals | 116–121 | 502 | 0.67(4H, d), 1.03–2.08(12H, m), 2.10–2.80(11H, m), 2.82–3.27(2H, m), 4.36(1H, s), 4.93(1H, b), 6.21–8.41(8H, m) |
| 58 | 4-F | 2-pyridyl | 2 | 10 | pale brown crystals | 112–117 | 530 | 0.69(4H, d), 1.03–2.05(16H, m), 2.09–2.77(11H, m), 2.87–3.27(2H, m), 4.37(1H, s), 4.95(1H, b), 6.73–8.53(8H, m) |

EXAMPLES 59 TO 63

Compounds of Table 12 below are prepared from various starting materials according to the same manner as described in Example 1 except using cyclopentylamine instead of ammonia.

TABLE 12

$$R_1-\text{C}_6H_4-\text{CHR}_2-\text{NH}-\text{[piperazine ring with (CH}_2\text{)}_a\text{]}-N-(CH_2)_n-SO_2NH-\text{cyclopentyl}$$

| Ex. No. | $R_1$ | $R_2$ | a | n | aspect | m.p. (°C.) | MS (M/Z)M⁺ | NMR δ (CDCl₃) ppm |
|---|---|---|---|---|---|---|---|---|
| 59 | 4-Cl | phenyl | 2 | 6 | pale yellow crystals | 86–90 | 517 | 1.13–2.72(26H, m), 3.02(2H, m)3.39–3.98(1H, m), 4.21 (1H, s)4.30(1H, b), 7.11–7.57(9H, m) |
| 60 | 4-F | 2-pyridyl | 2 | 4 | brown crystals | 128–132 | 474 | 1.30–2.13(12H, m), 2.17–3.31(12H, m)3.32–3.97(1H, m), 4.32(2H, b), 6.64–8.32(8H, m) |
| 61 | 4-F | 2-pyridyl | 2 | 6 | pale brown crystals | 123–128 | 502 | 1.22–2.80(26H, m), 2.81–3.28(2H, m)3.52–4.05(1H, m), 4.46(2H, b), 6.79–8.51(8H, m) |

TABLE 12-continued

R1-C6H4-CHN(R2)-(CH2)a-N-(CH2)n-SO2NH-cyclopentyl

| Ex. No. | R₁ | R₂ | a | n | aspect | m.p. (°C.) | MS (M/Z)M⁺ | NMR δ (CDCl₃) ppm |
|---|---|---|---|---|---|---|---|---|
| 62 | 4-F | 2-pyridyl | 2 | 8 | brown crystals | 128–132 | 530 | 0.93–2.75(30H, m), 2.76–3.16(2H, m)3.46–4.03(1H, m), 4.38(2H, b), 6.79–8.42(8H, m) |
| 63 | 4-F | 2-pyridyl | 2 | 10 | pale brown crystals | 119–123 | 558 | 1.01–2.77(34H, m), 2.78–3.18(2H, m)3.41–4.02(1H, m), 4.22(1H, b)4.37(1H, s), 6.69–8.55(8H, m) |

EXAMPLES 64 TO 86

Compounds of Table 13 below are prepared from various starting materials according to the same manner as described in Example 1 except using dimethylamine instead of ammonia.

TABLE 13

R1-C6H4-CHN(R2)-(CH2)a-N-(CH2)n-SO2N(CH3)2

| Ex. No. | R₁ | R₂ | a | n | aspect | m.p. (°C.) | MS (M/Z) M⁺ | NMR δ (CDCl₃) ppm |
|---|---|---|---|---|---|---|---|---|
| 64 | 4-Cl | phenyl | 2 | 6 | pale brown crystals | 93–96 | 477 | 1.12–2.08(8H, m), 2.22–2.63(10H, m) 2.72–3.12(2H, m), 2.83(6H, s), 4.16 (1H, s), 6.98–7.46(9H, m) |
| 65 | 4-F | 4-F-phenyl | 2 | 6 | pale brown crystals | 131–136 | 479 | 1.18–2.06(8H, m), 2.08–2.63(10H, m) 2.72–3.12(2H, m), 2.84(6H, s), 4.21 (1H, s), 6.71–7.57(8H, m) |
| 66 | 4-Cl | 4-pyridyl | 2 | 6 | pale brown crystals | 103–107 | 478 | 1.14–2.12(8H, m), 2.16–2.69(10H, m) 2.70–3.14(2H, m), 2.85(6H, s), 4.21 (1H, s), 7.19–8.47(8H, m) |
| 67 | H | 2-pyridyl | 2 | 6 | yellow crystals | 105–110 | 444 | 1.19–2.07(8H, m), 2.08–2.68(10H, m) 2.70–3.07(2H, m), 2.84(6H, s), 4.41 (1H, s), 6.87–8.45(9H, m) |
| 68 | 4-F | phenyl | 2 | 6 | pale brown crystals | 119–123 | 461 | 1.15–2.08(8H, m), 2.09–2.68(10H, m) 2.69–3.04(2H, m), 2.82(6H, s), 4.18 (1H, s), 6.73–7.55(9H, m) |
| 69 | 2-F | " | 2 | 8 | pale brown crystals | 93–96 | 489 | 1.03–2.03(12H, m), 2.04–2.57(10H, m) 2.60–2.95(2H, m), 3.03(6H, s), 4.49 (1H, s), 6.50–7.72(9H, m) |
| 70 | 4-CH₃ | " | 2 | 6 | colorless crystals | 143–147 | 457 | 1.16–2.12(8H, m), 2.26(3H, s) 2.36–3.10(12H, m), 2.83(6H, s), 4.21 (1H, s), 6.90–7.50(9H, m) |

TABLE 13-continued

Structure: R₁-phenyl-C(R₂)(H)-NH-(CH₂)a-N(piperazine-like)-(CH₂)n-SO₂N(CH₃)₂

| Ex. No. | R₁ | R₂ | a | n | aspect | m p. (°C.) | MS (M/Z) M⁺ | NMR δ (CDCl₃) ppm |
|---|---|---|---|---|---|---|---|---|
| 71 | 4-F | 3-pyridyl | 2 | 6 | pale brown crystals | 129–134 | 462 | 1.17–2.10(8H, m), 2.14–2.71(10H, m) 2.72–3.12(2H, m), 2.84(6H, s), 4.29 (1H, s), 6.69–8.72(8H, m) |
| 72 | 4-CF₃ | phenyl | 2 | 6 | pale brown crystals | 107–112 | 511 | 1.10–2.11(8H, m), 2.13–2.67(10H, m) 2.71–3.13(2H, m), 2.85(6H, s), 4.27 (1H, s), 7.09–7.61(9H, m) |
| 73 | 3-CF₃ | " | 2 | 8 | pale brown crystals | 98–102 | 539 | 1.09–2.08(12H, m), 2.14–2.63(10H, m) 2.68–3.10(2H, m), 2.80(6H, s), 4.21 (1H, s), 6.94–7.61(9H, m) |
| 74 | 4-MeO | " | 2 | 6 | brown crystals | 124–129 | 473 | 1.10–2.09(8H, m), 2.11–2.66(10H, m) 2.68–3.08(2H, m), 2.83(6H, s), 3.71 (3H, s), 4.16(1H, s), 6.61–7.51(9H, m) |
| 75 | 4-NO₂ | " | 2 | 6 | brown crystals | 112–117 | 488 | 1.17–2.10(8H, m), 2.14–2.71(10H, m) 2.72–3.12(2H, m), 2.84(6H, s), 4.29 (1H, s), 7.08–8.27(9H, m) |
| 76 | H | 3,4-dichlorophenyl | 2 | 6 | colorless crystals | 157–161 | 511 | 1.14–2.07(8H, m), 2.08–2.61(10H, m) 2.69–3.08(2H, m), 2.81(6H, s), 4.14 (1H, s), 7.01–7.47(8H, m) |
| 77 | 4-F | 2-pyridyl | 3 | 6 | brown crystals | 106–110 | 476 | 1.08–2.31(10H, m), 2.40–3.20(18H, m) 4.76(1H, s), 6.71–8.59(8H, m) |
| 78 | 4-Cl | 4-chlorophenyl | 2 | 8 | pale yellow crystals | 99–104 | 539 | 1.14–2.06(12H, m), 2.15–2.70(10H, m) 2.73–3.12(2H, m), 2.88(6H, s) 4.21(1H, s), 7.12–7.54(8H, m) |
| 79 | 4-F | 2-pyridyl | 2 | 2 | pale yellow crystals | 110–114 | 406 | 2.23–2.81(10H, m), 2.82–3.39(2H, m) 2.89(6H, s), 4.97(1H, s) 6.89–8.60(8H, m) |
| 80 | " | " | 2 | 3 | pale brown crystals | 103–108 | 420 | 1.79–2.28(2H, m), 2.30–2.73(10H, m) 2.83–3.20(2H, m), 2.88(6H, s), 4.44 (1H, s), 6.81–8.55(8H, m) |
| 81 | " | " | 2 | 5 | yellow crystals | 112–117 | 448 | 1.19–2.18(6H, m), 2.19–2.75(10H, m) 2.78–3.16(2H, m), 2.91(6H, s), 4.49 (1H, s), 6.77–8.58(8H, m) |
| 82 | " | " | 2 | 6 | yellow crystals | 142–147 | 462 | 1.10–2.07(8H, m), 2.12–2.73(10H, m) 2.74–3.09(2H, m), 2.88(6H, s), 4.47 (1H, s), 6.79–8.59(8H, m) |
| 83 | " | " | 2 | 7 | brown crystals | 121–126 | 476 | 1.10–2.02(10H, m), 2.08–2.62(10H, m) 2.69–3.11(2H, m), 2.79(6H, s), 4.32 (1H, s), 6.61–8.31(8H, m) |
| 84 | " | 2-pyridyl | 2 | 8 | yellow crystals | 127–131 | 490 | 1.13–2.01(12H, m), 2.04–2.63(10H, m) 2.24–3.23(2H, m), 2.84(6H, s), 4.40 (1H, s), 6.80–8.53(8H, m) |
| 85 | 4-F | " | 2 | 10 | brown crystals | 118–122 | 518 | 1.15–2.20(16H, m), 2.20–2.72(10H, m) 2.72–3.10(2H, m), 2.89(6H, s), 4.45 (1H, s), 6.70–8.53(8H, m) |
| 86 | " | " | 2 | 12 | yellow crystals | 110–115 | 546 | 1.14–2.21(20H, m), 2.30–2.79(8H, m) 2.80–3.20(2H, m), 2.91(6H, s), 3.41–3.77 (2H, m) 4.49(1H, m), 6.83–8.59(8H, m) |

EXAMPLES 87 TO 93

Compounds of Table 14 below are prepared from various starting materials according to the same manner as described in Example 1 except using aniline instead of ammonia.

TABLE 14

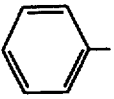

| Ex. No. | R₁ | R₂ | a | n | aspect | m p. (°C.) | MS (M/Z) M⁺ | NMR δ (CDCl₃) ppm |
|---|---|---|---|---|---|---|---|---|
| 87 | 4-Cl | phenyl | 2 | 6 | pale yellow crystals | 91–95 | 525 | 1.13–2.08(8H, m), 2.09–2.65(10H, m) 2.88–3.27(2H, m), 4.13(1H, s), 4.95 (1H, b), 6.98–7.50(14H, m) |
| 88 | 4-F | 2-pyridyl | 2 | 3 | pale yellow crystals | 106–110 | 468 | 1.72–2.18(2H, m), 2.18–2.81(10H, m) 3.19(2H, t), 4.34(1H, s) 6.44–8.54(13H, m) |
| 89 | " | " | 2 | 5 | colorless crystals | 138–142 | 496 | 1.16–2.09(6H, m), 2.10–2.81(10H, m) 2.92–3.26(2H, m), 4.42(1H, s), 4.64 (1H, b), 6.75–8.53(13H, m) |
| 90 | " | " | 2 | 6 | pale brown crystals | 123–129 | 510 | 1.01–2.05(8H, m), 2.06–2.70(10H, m) 3.07(2H, m), 4.40(1H, s), 5.44(1H, b) 6.67–8.48(13H, m) |
| 91 | " | " | 2 | 7 | pale brown crystals | 113–118 | 524 | 1.02–2.06(10H, m), 2.07–2.69(10H, m) 2.89–3.26(2H, m), 4.22(1H, b) |
| 92 | " | " | 2 | 8 | pale brown crystals | 130–134 | 538 | 1.02–2.09(12H, m), 2.11–2.66(10H, m) 2.83–3.26(2H, m), 4.39(1H, s) 4.97(1H, b) 6.42–8.43(13H, m) |
| 93 | " | " | 2 | 10 | brown crystals | 117–122 | 566 | 0.90–2.11(16H, m), 2.13–2.71(10H, m) 2.91–3.25(2H, m), 4.39(1H, s) 5.28(1H, b) 6.72–8.43(13H, m) |

EXAMPLES 94 TO 97

Compounds of Table 15 below are prepared from various starting materials according to the same manner as described in Example 1 except using o-aminophenol instead of ammonia.

TABLE 15

| Ex. No. | R₁ | R₂ | a | n | aspect | m p. (°C.) | MS (M/Z) M⁺ | NMR δ (CDCl₃) ppm |
|---|---|---|---|---|---|---|---|---|
| 94 | 4-Cl | phenyl | 2 | 6 | colorless crystals | 106–110 | 541 | 1.07–2.05(8H, m), 2.31–3.23(12H, m) 4.22(1H, s), 6.64–7.61(15H, m) |
| 95 | 4-F | 2-pyridyl | 2 | 4 | brown crystals | 103–107 | 498 | 1.37–2.22(4H, m), 2.35–3.26(12H, m) 4.46(1H, s), 6.35–8.67(14H, m) |
| 96 | " | " | 2 | 6 | yellow crystals | 128–133 | 526 | 0.90–2.20(8H, m), 2.45–3.31(12H, m) 4.51(1H, s), 6.21(2H, b) 6.58–8.61(12H, m) |

TABLE 15-continued

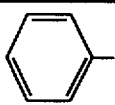

| Ex. No. | R₁ | R₂ | a | n | aspect | m p. (°C.) | MS (M/Z) M⁺ | NMR δ (CDCl₃) ppm |
|---|---|---|---|---|---|---|---|---|
| 97 | H | (phenyl) | 2 | 8 | brown crystals | 134–139 | 535 | 0.87–2.11(12H, m), 2.12–3.32(12H, m) 4.14(1H, s), 6.16(2H, b) 6.52–7.63(14H, m) |

EXAMPLES 98 TO 100

Compounds of Table 16 below are prepared from various starting materials according to the same manner as described in Example 1 except using $R_3$—$NH_2$ instead of ammonia.

TABLE 16

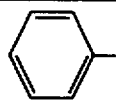

| Ex. No. | R₁ | R₂ | a | n | R₃ (R₄ = H) | aspect | (°C.) | MS (M/Z)M⁺ | NMR δ(CDCl₃) ppm |
|---|---|---|---|---|---|---|---|---|---|
| 98 | 4-Cl | (phenyl) | 2 | 6 | (3,4,5-tri-OMe phenyl) | brown crystals | 105–109 | 615 | 1.20–2.12(8H, m), 2.56–2.86 (12H, m), 3.74(3H, s), 3.78(6H, s), 4.26(1H, s) 6.95–7.48(12H, m) |
| 99 | H | " | 2 | 6 | " | pale brown crystals | 109–113 | 581 | 1.14–2.15(8H, m), 2.52–3.28 (12H, m), 3.77(3H, s), 3.80 (6H, s), 4.29(1H, s), 6.41–6.87 (1H, b), 6.69(2H, s) 7.04–7.59(10H, m) |
| 100 | 4-Cl | " | 2 | 6 | (3,5-di-CMe₃-4-OH phenyl) | pale brown crystals | 231–234 | 653 | 1.15–2.32(26H, m), 2.62–3.38 (12H, m), 4.32(1H, s), 5.10(1H, b), 7.07–7.47(11H, m) |

EXAMPLE 101

Compound of Table 17 below is prepared from corresponding starting material according to the same manner as described in Example 1 except using β-aminoethyl alcohol instead of ammonia.

TABLE 17

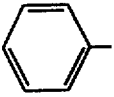

| Ex. No. | R₁ | R₂ | a | n | aspect | m p. (°C.) | MS (M/Z) M⁺ | NMR δ (CDCl₃) ppm |
|---|---|---|---|---|---|---|---|---|
| 101 | 4-Cl | (phenyl) | 2 | 6 | colorless crystals | 125–130 | 494 | 1.14–2.06(8H, m), 2.13–2.62(10H, m) 2.76–3.42(5H, m), 3.54–3.88(3H, m) 4.16(1H, s), 7.04–7.54(9H, m) |

EXAMPLE 102

(Method B)

Preparation of 3-[4-[4-fluorophenyl-(2-pyridyl)methyl]-1-piperazinyl]propylsulfonyl methylethylamine hydrochloride 3-Chloropropanesulfonyl chloride (2.54 g) is dissolved in methylene chloride and isopropylamine (1.90 g) is added dropwise under ice cooling. After stirring at room temperature for 2 hours, the solution is extracted with methylene chloride and water to give crude 3-chloropropanesulfonyl methylethylamine (2.54 g, 89%) as pale yellow liquid.

The above compound (2.54 g), [4-fluorophenyl-(2-pyridyl)methyl]piperazine (4.14 g) and triethylamine (1.54 g) are dissolved in toluene. After refluxing for 48 hours, water is added to the mixture and the toluene layer is separated and dried over anhydrous magnesium sulfate. The filtrate is concentrated under reduced pressure to give brown liquid. The liquid is treated by column chromatography [silica gel, chloroform-methanol (20:1)] and the resulting purified material (4.49 g, 81%) is converted into hydrochloride by using hydrochloric acid-methanol solution and recrystallized from ethanol-diethyl ether to give the title compound as pale yellow crystals. mp.137°–142° C.

Mass Spectrum (MS): m/z:434(M⁺);

NMR Spectrum: δ(CDCl₃) ppm: 1.21 (6H, d), 1.66–2.26 (2H, m), 2.26–2.76 (10H, m), 3.10 (2H, t), 3.66 (1 H, q), 4.46 (1 H, s), 4.60–4.96 (1 H, b), 6.82–8.66 (8H, m).

EXAMPLE 103

(Method C)

Preparation of 6-[4-[4-fluorophenyl-(2-pyridyl)methyl]-1-piperazinyl]hexylsulfonyl dimethylamine, hydrochloride 6-(1-Piperazinyl)hexylsulfondimethylamine (1.5 g) and triethylamine (0.6 g) are added to a flask and dissolved in isopropanol (50 ml) and a solution of [4-fluorophenyl-(2-pyridyl)methyl] chloride (1.3 g) in isopropanol is added dropwise. After stirring at room temperature for 16 hours, the solution is refluxed for 2 hours. The reaction mixture is concentrated under reduced pressure and extracted with chloroform and water. The chloroform layer is separated and dried over anhydrous magnesium sulfate. The filtrate is concentrated under reduced pressure to give brown liquid. The liquid is treated by column chromatography [silica gel, chloroform-methanol (20:1)] and the resulting purified material (0.6 g, 24%) is converted into hydrochloride by using hydrochloric acid-methanol solution and recrystallized from ethanol-diethyl ether to give the title compound as pale yellow crystals. mp.142°–147° C.

Mass Spectrum (MS): m/z:462(M⁺);

NMR Spectrum: δ(CDCl₃) ppm: 1.10–2.07 (8H, m), 2.12–2.73 (10H, m), 2.74–3.09 (2H, m), 2.88 (6H, s), 4.47 (1 H, s), 6.79–8.59 (8H, m).

EXAMPLES 104 AND 105

Compounds of Table 18 below are prepared from corresponding starting materials according to the same manner as described in Example 1.

TABLE 18

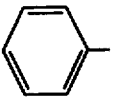

| Ex. No. | R₁ | R₂ | a | n | aspect | m p. (°C.) | MS (M/Z)M⁺ | NMR δ (CDCl₃) ppm |
|---|---|---|---|---|---|---|---|---|
| 104 | 4-Cl | (phenyl) | 2 | 10 | colorless crystals | 176–178 | 505 | 1.04–1.67(16H, m), 2.12–2.76(10H, m) 2.97–3.31(2H, m), 4.28(1H, s), 4.48–5.00(2H, b), 7.20–7.64(9H, m) |
| 105 | " | " | 2 | 12 | colorless crystals | 156–161 | 533 | 1.08–2.04(20H, m), 2.13–2.63(10H, m) 2.84–3.22(2H, m), 4.18(1H, s), 4.39–4.88(2H, b), 7.08–7.57(9H, m) |

EXAMPLE 106

Compound of Table 19 below is prepared from corresponding starting material according to the same manner as described in Example 1 except using methylamine instead of ammonia.

TABLE 19

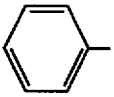

| Ex. No. | $R_1$ | $R_2$ | a | n | aspect | m p. (°C.) | MS (M/Z)$M^+$ | NMR δ ($CDCl_3$) ppm |
|---|---|---|---|---|---|---|---|---|
| 106 | 4-Cl | ⌬ | 2 | 5 | pale yellow crystals | 105–109 | 449 | 1.20–2.11(6H, m), 2.18–2.66(10H, m) 2.75(3H, s), 2.70–3.22(2H, m), 4.20 (1H, s), 4.34–4.72(1H, b), 7.02–7.56 (9H, m) |

EXAMPLES 107 AND 108

Compounds of Table 20 below are prepared from corresponding starting materials according to the same manner as described in Example 1 except using ethylamine instead of ammonia.

TABLE 20

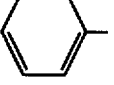

| Ex. No. | $R_1$ | $R_2$ | a | n | aspect | m p. (°C.) | MS (M/Z)$M^+$ | NMR δ ($CDCl_3$) ppm |
|---|---|---|---|---|---|---|---|---|
| 107 | 4-Cl | ⌬ | 2 | 7 | pale yellow crystals | 91–95 | 491 | 1.17(3H, t), 1.01–2.05(10H, m), 2.09– 2.76(10H, m), 2.77–3.45(4H, m), 4.19 (1H, s), 4.39(1H, b), 7.06–7.64(9H, m) |
| 108 | " | " | 2 | 8 | pale yellow crystals | 89–93 | 505 | 1.20(3H, t), 0.99–2.16(12H, m) 2.25– 2.81(10H, m), 2.82–3.43(4H, m), 4.22 (1H s), 4.36–4.87(1H, b), 7.07–7.58 (9H, m) |

EXAMPLE 109

Compound of Table 21 below is prepared from corresponding starling material according to the same manner as described in Example 1 except using propylamine instead of ammonia.

TABLE 21

Structure: R₁-phenyl-CHN(R₂)-[piperidine ring with (CH₂)ₐ]-N-(CH₂)ₙ-SO₂NHC₃H₇-(n)

| Ex. No. | R₁ | R₂ | a | n | aspect | m.p. (°C.) | MS (M/Z)M⁺ | NMR δ (CDCl₃) ppm |
|---|---|---|---|---|---|---|---|---|
| 109 | 4-Cl | phenyl | 2 | 10 | colorless crystals | 134–136 | 547 | 0.90(3H, t), 1.09–1.99(18H, m), 2.10–2.64(10H, m), 2.73–3.28(4H, m), 4.18 (1H, s), 4.09–4.57(1H, b), 6.99–7.54 (9H, m) |

EXAMPLES 110 AND 111

Compounds of Table 22 below are prepared from corresponding starting materials according to the same manner as described in Example 1 except using isopropylamine instead of ammonia.

TABLE 22

Structure: R₁-phenyl-CHN(R₂)-[piperidine with (CH₂)ₐ]-N-(CH₂)n-SO₂NHCH(CH₃)₂

| Ex. No. | R₁ | R₂ | a | n | aspect | m.p. (°C.) | MS (M/Z)M⁺ | NMR δ(CDCl₃) ppm |
|---|---|---|---|---|---|---|---|---|
| 110 | 4-Cl | phenyl | 2 | 5 | pale yellow crystals | 101–105 | 477 | 1.19(6H, d), 1.04–2.11(6H, m), 2.17–2.75(10H, m), 2.76–3.14(2H, m), 3.63 (1H, q), 4.16(1H, s), 4.25(1H, s), 7.01–7.54(9H, m) |
| 111 | " | " | 2 | 8 | pale yellow crystals | 85–89 | 519 | 1.25(6H, d), 1.15–2.20(12H, m), 2.34–3.22(12H, m)3.38–3.91(1H, m), 4.27 (1H, s), 4.41(1H, d), 7.06–7.50(9H, m) |

EXAMPLES 112 TO 126

Compounds of Table 23 below are prepared from corresponding starting materials according to the same manner as described in Example 1 except using cyclopropylamine instead of ammonia.

TABLE 23

Structure: R₁-phenyl-CHN(R₂)-[piperidine with (CH₂)ₐ]-N-(CH₂)ₙ-SO₂NH-cyclopropyl

| Ex. No. | R₁ | R₂ | a | n | aspect | m.p. (°C.) | MS (M/Z)M⁺ | NMR δ (CDCl₃) ppm |
|---|---|---|---|---|---|---|---|---|
| 112 | 4-Cl | phenyl | 2 | 3 | pale brown crystals | 137–142 | 447 | 0.65(4H, d), 1.58–2.78(13H, m), 3.15 (2H, t), 4.21(1H, s), 5.48–6.00(1H, b) 6.98–7.52(9H, m) |
| 113 | " | " | 2 | 4 | pale brown | 136–141 | 461 | 0.63(4H, d), 1.21–1.99(4H, m), 2.08–2.71(11H, m), 3.05(2H, t), 4.18(1H, s) |

TABLE 23-continued

Structure: R1-phenyl-CH(R2)-N(piperidine with (CH2)a)-N-(CH2)n-SO2NH-cyclopropyl

| Ex. No. | R1 | R2 | a | n | aspect | m.p. (°C.) | MS (M/Z)M+ | NMR δ (CDCl3) ppm |
|---|---|---|---|---|---|---|---|---|
| 114 | " | " | 2 | 5 | pale brown crystals | 125–130 | 475 | 5.01(1H, b), 6.99–7.50(9H, m) 0.66(4H, d), 1.13–2.02(6H, m), 2.14–2.73(11H, m), 2.73–3.25(2H, m), 4.23 (1H, s), 5.12(1H, b), 7.03–7.57(9H, m) |
| 115 | " | " | 2 | 7 | pale brown crystals | 122–127 | 503 | 0.69(4H, d), 1.08–1.98(10H, m), 2.11–2.77(11H, m), 2.86–3.27(2H, m), 4.22 (1H, s), 4.86(1H, b), 6.98–7.56(9H, m) |
| 116 | " | " | 2 | 8 | pale brown crystals | 117–123 | 517 | 0.67(4H, d), 1.09–2.76(23H, m), 2.88–3.27(2H, m), 4.22(1H, s), 5.05–5.41 (1H, b), 7.08–7.57(9H, m) |
| 117 | " | " | 2 | 9 | pale yellow crystals | 109–115 | 531 | 0.54(4H, d), 0.89–1.99(14H, m), 2.00–2.59(11H, m), 2.72–3.16(2H, m), 4.11 (1H, s), 4.75(1H, b), 6.99–7.48(9H, m) |
| 118 | " | " | 2 | 10 | pale yellow crystals | 105–109 | 545 | 0.69(4H, d), 0.97–1.96(16H, m), 2.02–2.73(11H, m), 2.83–3.28(2H, m), 4.20 (1H, s), 4.91(1H, b), 7.01–7.54(9H, m) |
| 119 | " | " | 2 | 12 | yellow crystals | 104–109 | 573 | 0.66(4H, d), 0.93–1.97(20H, m), 1.99–2.69(11H, m), 2.78–3.20(2H, m), 4.10 (1H, s), 4.71(1H, b), 6.87–7.37(9H, m) |
| 120 | 3-Cl | " | 2 | 6 | colorless crystals | 169–176 | 489 | 0.65(4H, d), 1.11–1.99(8H, m), 2.08–2.73(11H, m), 4.19(1H, s), 4.62(1H, s) 7.02–7.51(9H, m) |
| 121 | 2-Cl | phenyl | 2 | 6 | colorless crystals | 123–129 | 489 | 0.65(4H, d), 1.11–1.93(8H, m), 2.07–2.69(11H, m), 2.84–3.16(2H, m), 4.68–5.02(1H, b), 4.77(1H, s), 6.89–7.84 (9H, m) |
| 122 | 4-Cl | 2-pyridyl | 2 | 6 | yellow crystals | 106–111 | 490 | 0.65(4H, d), 1.02–2.68(18H, m), 2.82–3.26(3H, m), 4.44(1H, s), 5.52–5.87 (1H, b), 6.85–8.63(8H, m) |
| 123 | H | " | 2 | 6 | yellow crystals | 69–81 | 456 | 0.66(4H, d), 1.12–2.04(8H, m), 2.09–2.72(11H, m), 3.15(2H, t), 4.42(1H, s) 4.61(H, s), 6.85–8.56(9H, m) |
| 124 | 4-F | phenyl | 2 | 6 | pale yellow crystals | 115–119 | 473 | 0.68(4H, d), 1.22–1.98(8H, m), 2.26–2.61(11H, m), 3.01–3.12(2H, m), 4.21 (1H, s), 4.62(1H, b), 6.88–7.42(9H, m) |
| 125 | " | 4-F-phenyl | 2 | 6 | colorless crystals | 184–187 | 491 | 0.68(4H, d), 1.18–3.33(21H, m), 4.36 (1H, s), 6.30(1H, b), 6.69–7.59(8H, m) |
| 126 | H | phenyl | 2 | 6 | pale brown crystals | 128–133 | 455 | 0.66(4H, d), 1.12–2.15(8H, m), 2.24–3.34(13H, m), 4.32(1H, s), 6.60(1H, b) 7.02–7.58(10H, m) |

EXAMPLES 127 TO 134

Compounds of Table 24 below are prepared from corresponding starting materials according to the same manner as described in Example 1 except using cyclobutylamine instead of ammonia.

TABLE 24

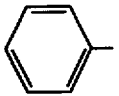

| Ex. No. | R₁ | R₂ | a | n | aspect | m.p. (°C.) | MS (M/Z)M⁺ | NMR δ (CDCl₃) ppm |
|---|---|---|---|---|---|---|---|---|
| 127 | 4-Cl | 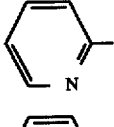 | 2 | 5 | pale yellow crystals | 114–118 | 489 | 1.19–2.60(22H, m), 2.73–3.20(2H, m) 3.44–4.00(1H, m), 4.21(1H, s), 4.81 (1H, d), 7.03–7.52(9H, m) |
| 128 | " | " | 2 | 6 | pale yellow crystals | 117–121 | 503 | 0.96–2.55(24H, m), 2.67–3.06(2H, m) 3.55–4.07(1H, m), 4.15(1H, s), 4.75 (1H, d), 6.96–7.48(9H, m) |
| 129 | " | " | 2 | 7 | pale yellow crystals | 118–124 | 517 | 0.96–2.60(26H, m), 2.69–3.10(2H, m) 3.55–4.03(1H, m), 4.19(1H, s), 4.78 (1H, d), 6.96–7.52(9H, m) |
| 130 | " | " | 2 | 8 | colorless crystals | 106–112 | 531 | 1.03–2.65(28H, m), 2.74–3.25(2H, m) 3.68–4.08(1H, m), 4.22(1H, s), 4.75 (1H, d), 7.06–7.55(9H, m) |
| 131 | 3-Cl | " | 2 | 6 | colorless crystals | 129–135 | 503 | 1.10–2.67(24H, m), 2.77–3.16(2H, m) 3.51–4.04(1H, m), 4.22(1H, s), 4.65 (1H, d), 7.07–7.60(9H, m) |
| 132 | 2-Cl | " | 2 | 6 | pale yellow crystals | 121–127 | 503 | 1.12–2.61(24H, m), 2.71–3.19(2H, m) 3.53–4.00(1H, m), 4.80(1H, s), 5.11–5.58(1H, b), 6.91–7.93(9H, m) |
| 133 | 4-F | 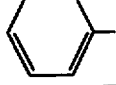 | 2 | 6 | yellow crystals | 98–105 | 488 | 1.14–3.09(26H, m), 3.60–4.15(1H, m) 4.44(1H, s), 5.39(1H, d), 6.65–8.60 (8H, m) |
| 134 | H |  | 2 | 6 | yellow crystals | 123–127 | 469 | 1.20–2.62(24H, m), 2.72–3.13(2H, m) 3.54–3.99(1H, m), 4.21(1H, s), 5.07 (1H, d), 6.93–7.52(10H, m) |

EXAMPLES 135 TO 141

Compounds of Table 25 below are prepared from various starting materials according to the same manner as described in Example 1 except using cyclopentylamine instead of ammonia.

TABLE 25

| Ex. No. | R₁ | R₂ | a | n | aspect | m.p. (°C.) | MS (M/Z)M⁺ | NMR δ (CDCl₃) ppm |
|---|---|---|---|---|---|---|---|---|
| 135 | 4-Cl | | 2 | 4 | yellow crystals | 127–133 | 489 | 1.24–2.58(22H, m), 2.82–3.24(24H, m) 3.49–3.97(1H, m), 4.22(1H, s), 4.41 (1H, d), 7.04–7.52(9H, m) |
| 136 | " | " | 2 | 5 | pale yellow crystals | 125–129 | 503 | 1.07–2.65(24H, m), 2.86–3.21(2H, m) 3.42–3.98(1H, m), 4.21(1H, s), 4.47 (1H, d), 7.04–7.57(9H, m) |
| 137 | " | " | 2 | 7 | pale brown crystals | 116–122 | 531 | 1.10–2.64(28H, m), 2.79–3.24(2H, m) 3.49–4.00(1H, b), 4.22(1H, s), 4.49 (1H, d), 7.04–7.56(9H, m) |
| 138 | " | " | 2 | 8 | pale brown | 109–112 | 545 | 0.98–2.46(30H, m), 2.64–3.03(2H, m) 3.28–3.80(1H, m), 4.06(1H, s), 4.31 |

TABLE 25-continued

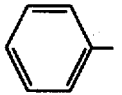

| Ex. No. | $R_1$ | $R_2$ | a | n | aspect | m p. (°C.) | MS (M/Z)M+ | NMR δ (CDCl₃) ppm |
|---|---|---|---|---|---|---|---|---|
| 139 | 3-Cl | " | 2 | 6 | yellow crystals | 115–120 | 517 | (1H, d), 6.94–7.47(9H, m) 1.14–2.62(26H, m), 2.80–3.20(2H, m) 3.43–3.87(1H, m), 4.12–4.45(1H, b) 4.20(1H, s), 7.03–7.51(9H, m) |
| 140 | 2-Cl | " | 2 | 6 | colorless crsytals | 108–115 | 517 | 1.12–2.63(26H, m), 2.72–3.15(2H, m) 3.42–3.88(1H, m), 4.71–5.20(1H, b) 4.79(1H, s), 6.92–7.89(9H, m) |
| 141 | H | " | 2 | 6 | pale yellow crystals | 123–128 | 483 | 1.11–2.15(16H, m), 2.16–2.62(10H, m) 2.79–3.19(2H, m), 3.46–3.87(1H, m) 4.25(1H, s), 4.72–5.19(1H, b), 7.05–7.58(10H, m) |

EXAMPLES 142 TO 149

Compounds of Table 26 below are prepared from various starting materials according to the same manner as described in Example 1 except using cyclohexylamine instead of ammonia.

TABLE 26

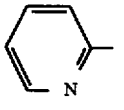

| Ex. No. | $R_1$ | $R_2$ | a | n | aspect | m p. (°C.) | MS (M/Z)M+ | NMR δ (CDCl₃) ppm |
|---|---|---|---|---|---|---|---|---|
| 142 | 4-Cl | 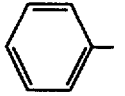 | 2 | 5 | pale yellow crystals | 132–128 | 517 | 0.96–2.54(26H, m), 2.79–3.45(3H, m) 4.19(1H, s), 4.41(1H, d), 7.05–7.49 (9H, m) |
| 143 | " | " | 2 | 6 | pale yellow crystals | 126–131 | 531 | 0.94–2.54(28H, m), 2.81–3.33(3H, m) 4.20(1H, s), 4.34(1H, b), 7.04–7.48 (9H, m) |
| 144 | " | " | 2 | 7 | pale yellow crystals | 119–124 | 545 | 0.96–2.55(30H, m), 2.70–3.24(3H, m) 4.19(1H, s), 4.33(1H, d), 7.04–7.50 (9H, m) |
| 145 | " | " | 2 | 8 | colorless crystals | 122–126 | 559 | 1.01–2.58(32H, m), 2.83–3.34(3H, m) 4.21(1H, s), 4.32(1H, d), 7.06–7.52 (9H, m) |
| 146 | 3-Cl | " | 2 | 6 | pale brown crystals | 118–124 | 531 | 0.80–2.65(28H, m), 2.79–3.17(3H, m) 4.19(1H, s), 4.31(1H, s), 7.03–7.54 (9H, m) |
| 147 | 2-Cl | " | 2 | 6 | pale yellow crystals | 131–136 | 531 | 1.02–2.19(28H, m), 2.81–3.46(3H, m) 4.30(1H, d), 4.82(1H, s), 6.99–7.92 (9H, m) |
| 148 | 4-F | pyridyl | 2 | 6 | yellow crystals | 115–125 | 516 | 0.94–2.70(28H, m), 2.78–3.74(3H, m) 4.45(1H, s), 5.18(1H, d), 6.70–8.58 (8H, m) |
| 149 | H | phenyl | 2 | 6 | pale yellow crystals | 127–135 | 497 | 0.96–2.09(18H, m), 2.12–2.60(10H, m) 2.74–3.16(2H, m), 3.31–3.74(1H, m) 4.24(1H, s), 4.76(1H, d), 7.07–7.58 (10H, m) |

EXAMPLES 150 TO 152

Compounds of Table 27 below are prepared from various starting materials according to the same manner as described in Example 1 except using dimethylamine instead of ammonia.

TABLE 27

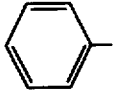

| Ex. No. | $R_1$ | $R_2$ | a | n | aspect | m.p. (°C.) | MS (M/Z)M+ | NMR δ(CDCl$_3$) ppm |
|---|---|---|---|---|---|---|---|---|
| 150 | 4-Cl | (phenyl) | 2 | 7 | pale brown crystals | 86–89 | 491 | 1.11–2.09(12H, m), 2.10–2.64(8H, m) 2.70–3.15(8H, m), 4.21(1H, s), 7.06–7.55(9H, m) |
| 151 | " | " | 2 | 10 | pale yellow crystals | 95–98 | 533 | 1.05–2.16(16H, m), 2.10–2.68(10H, m) 2.71–3.29(8H, m), 4.19(1H, s), 7.03–7.60(9H, m) |
| 152 | " | " | 2 | 12 | colorless crystals | 133–137 | 561 | (CDCl$_3$ + CD$_3$OD)1.17–2.12(20H, m), 2.62–3.93(18H, m), 4.45(1H, s), 7.20–7.92(9H, m) |

EXAMPLE 153

Preparation of potassium 6-[[4-(4-chlorophenyl)phenylmethyl]-1-piperazinyl]hexylsulfonamide 6-[[4-(4-Chlorophenyl)phenylmethyl]-1-piperazinyl]hexylsulfonamide prepared according to Method A is converted into potassium salt using aqueous potassium hydroxide solution or potassium tert-butoxide and recrystallized from methanol-diethyl ether to give the title compound as colorless crystals.

mp.214°–217° C.

NMR Spectrum: δ(CDCl$_3$) ppm: 1.12–2.08 (8H, m), 2.43–3.53 (12H, m), 4.28 (1H, s), 5.25 (1H, s), 7.01–7.42 (9H, m).

We claim:

1. A diazacycloalkanealkylsulfonamide compound having the following formula I:

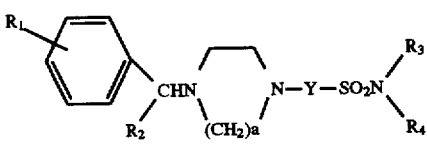

wherein $R_1$ is hydrogen atom, alkyl having 1 to 4 carbon atoms, alkoxy having 1 to 4 carbon atoms, halogen atom, hydroxy, trifluoromethyl, nitro or amino; $R_2$ is phenyl which may optionally be substituted by one to three substituents on the phenyl ring selected from alkyl having 1 to 4 carbon atoms, alkoxy having 1 to 4 carbon atoms, halogen atom, hydroxy, trifluoromethyl, nitro and amino, or $R_2$ is 2-pyridyl, 3-pyridyl or 4-pyridyl; a is 2 or 3; Y is alkylene having 1 to 12 carbon atoms; and $R_3$ and $R_4$ are the same or different and are each hydrogen atom, alkyl having 1 to 4 carbon atoms, hydroxyalkyl having 1 to 4 carbon atoms or cycloalkyl having 3 to 8 carbon atoms, or phenyl which may optionally be substituted by one to three substituents on the phenyl ring selected from alkyl having 1 to 4 carbon atoms, alkoxy having 1 to 4 carbon atoms, halogen atom, hydroxy, trifluoromethyl, nitro and amino, or a pharmacologically acceptable salt thereof.

2. The compound of formula I as claimed in claim 1 wherein $R_1$ is hydrogen atom, alkyl having 1 to 4 carbon atoms, alkoxy having 1 to 4 carbon atoms, halogen atom, hydroxy, trifluoromethyl, nitro or amino; $R_2$ is unsubstituted phenyl, phenyl substituted by 1 to 2 halogen atoms, 2-pyridyl or 4-pyridyl; a is 2; Y is alkylene having 3 to 10 carbon atoms; and one of $R_3$ and $R_4$ is hydrogen atom and the other is hydrogen atom, alkyl having 1 to 4 carbon atoms, hydroxyalkyl having 1 to 4 carbon atoms, cycloalkyl having 3 to 8 carbon atoms, unsubstituted phenyl or phenyl which is substituted by one to three substituents on the phenyl ring selected from hydroxy and alkoxy having 1 to 4 carbon atoms; or both of $R_3$ and $R_4$ are alkyl having 1 to 4 carbon atoms.

3. The compound of formula I as claimed in claim 1 wherein $R_1$ is hydrogen atom or halogen atom; $R_2$ is unsubstituted phenyl, phenyl substituted by halogen atom, 2-pyridyl or 4-pyridyl; a is 2; Y is alkylene having 3 to 10 carbon atoms; and one of $R_3$ and $R_4$ is hydrogen atom and the other is hydrogen atom, alkyl having 1 to 4 carbon atoms, hydroxyalkyl having 1 to 4 carbon atoms, cycloalkyl having 3 to 6 carbon atoms or tri($C_1$–$C_4$ alkoxy)-substituted phenyl; or both of $R_3$ and $R_4$ are alkyl having 1 to 4 carbon atoms.

4. The compound as claimed in claim 3 wherein $R_1$ is meta- or para-halogen atom and $R_2$ is unsubstituted phenyl, 4-fluorophenyl, 2-pyridyl or 4-pyridyl.

5. The compound as claimed in claim 4 wherein $R_1$ is meta- or para-chlorine atom; $R_2$ is unsubstituted phenyl.

6. The compound as claimed in claim 4 wherein $R_1$ is para-fluorine atom and $R_2$ is 2-pyridyl.

7. An agent for preventing or treating allergic disease comprising as an active ingredient one or more diazacycloalkanealkylsulfonamide compounds having the following formula:

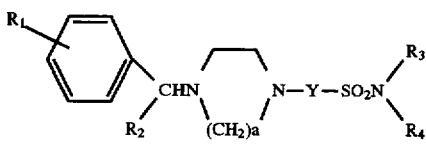

wherein $R_1$ is hydrogen atom, alkyl having 1 to 4 carbon atoms, alkoxy having 1 to 4 carbon atoms, halogen atom, hydroxy, trifluoromethyl, nitro or amino; $R_2$ is phenyl which may optionally be substituted by 1 to 3 substituents on the phenyl ring selected from alkyl having 1 to 4 carbon atoms, alkoxy having 1 to 4 carbon atoms, halogen atom, hydroxy, trifluoromethyl, nitro and amino, or $R_2$ is 2-pyridyl, 3-pyridyl or 4-pyridyl; a is 2 or 3; Y is alkylene having 1 to 12 carbon atoms; and $R_3$ and $R_4$ are the same or different and are each hydrogen atom, alkyl having 1 to 4 carbon atoms, hydroxyalkyl having 1 to 4 carbon atoms or cycloalkyl having 3 to 8 carbon atoms, or phenyl which may optionally be substituted by 1 to 3 substituents on the phenyl ring selected from alkyl having 1 to 4 carbon atoms, alkoxy having 1 to 4 carbon atoms, halogen atom, hydroxy, trifluoromethyl, nitro and amino, or a pharmacologically acceptable salt thereof, in combination with a pharmaceutically acceptable carrier.

8. A method for treatment or proplyaxis of an allergic disease comprising administering to a person an effective amount of the compound of claim 1.

9. The method as claimed in claim 8 wherein the allergic disease is bronchial asthma, allergic rhinitis, atopic dermatitis, or urticaria.

* * * * *